US007018626B2

(12) United States Patent
Strom et al.

(10) Patent No.: US 7,018,626 B2
(45) Date of Patent: Mar. 28, 2006

(54) CHIMERIC IL-10

(75) Inventors: Terry B. Strom, Brookline, MA (US); Xin Xiao Zheng, Brookline, MA (US); Alan Steele, Wellesley, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 269 days.

(21) Appl. No.: 10/145,517

(22) Filed: May 14, 2002

(65) Prior Publication Data

US 2003/0026778 A1     Feb. 6, 2003

Related U.S. Application Data

(63) Continuation of application No. 08/968,905, filed on Nov. 6, 1997, now Pat. No. 6,403,077, which is a continuation-in-part of application No. 08/355,502, filed on Dec. 12, 1994, now Pat. No. 6,410,008.

(51) Int. Cl.
*C07K 14/52*     (2006.01)
*A61K 38/20*     (2006.01)

(52) U.S. Cl. .................... 424/85.2; 530/351; 530/402; 514/2; 514/8; 514/12

(58) Field of Classification Search .............. 424/85.2; 530/351, 402; 514/2, 8, 12
See application file for complete search history.

(56) References Cited

U.S. PATENT DOCUMENTS

| | | | |
|---|---|---|---|
| 5,116,964 A | 5/1992 | Capon et al. | |
| 5,196,321 A | 3/1993 | Bachmair et al. | |
| 5,231,012 A | 7/1993 | Mosmann et al. | |

FOREIGN PATENT DOCUMENTS

| | | |
|---|---|---|
| CA | 2045869 | 6/1991 |
| EP | 04 64 533 | 1/1992 |
| FR | 2686899 | 1/1992 |
| WO | WO 90 07932 | 7/1990 |
| WO | WO 94 04180 | 3/1994 |
| WO | WO94/08606 | 4/1994 |

OTHER PUBLICATIONS

Laurence, D.R., "A Dictionary of Pharmacology and Allied Topics," p. 90 (1998).
Rabinovitch, A., "Immunoregulatory and Cytokine Imbalances in the Pathogenesis of IDDM," Diabetes, 43:613-621 (1994).
Steele, Alan W., et al. *Structure and function in vitro and in vivo of a family of murine interleukin-2Fc...* J. American Soc. Of Nephr. 4(3):636, 1993.
A. Traub, et al. *Inerferon albumin conjugate with conserved biological activity*, J. of General Virology 53:389-392, 1981.
Rene de Waal Malefyt, et al. *Interleukin 10 (IL-10) and Viral IL-10 Strongly Reduce Antigen-specific Human T Cell Proliferation by Diminishing the Antigen...* J. Exp. Med. 174:915-924, Oct., 1991.
Karl Byrne, et al. *Adult Respiratory Distress Syndrome.* Acute Care 13:206-234, 1987.
Roger C. Bone, M.D. *The Pathogenesis of Sepsis.* Annals of Internal Medicine, 115(6):457-469, Sep. 1991.
Catherine Gerard, et al. *Interleukin 10 Reduces the Release of Tumor Necrosis Factor and Prevents Lethality in Experimental Endotoxemia.* Journal of Experimental Medicine, 177(2):547-550, Feb. 1993.
David F. Fiorentino, et al. *IL-10 Acts on the Antigen-Presenting Cell to Inhibit Cytokine Production by Th1 Cells.* Journal of Immunology 146(10):3444-3451, May 1991.
David F. Fiorentino, et al. *IL-10 Inhibits Cytokine Production by Activated Macrophages.* Journal of Immunology 147(11):3815-3822, Dec. 1991.
Di-Hwei Hsu, et al. *Differential effects of IL-4 and IL-10 on IL-2-induced IFN-γ synthesis and lymphokine-activated killer activity.* International Immunology 4(5):563-569, 1992.
Myung-Shik Lee, et al. *Pancreatic Islet Production of Murine Interleukin-10 Does Not Inhibit Immune-mediated Tissue Destruction.* Journal of Clinical Investigation 93:1332-1338, 1994.
Kevin W. Moore, et al. *Homology of Cytokine Synthesis Inhibitory Factor (IL-10) to the Epstein-Barr Virus bene BCRFI.* Science 248:1230-1234, Jun. 1990.
Kevin W. Moore, et al. *Interleukin-10.* Annual Review of Immunology 11:165-190, 1993.
LuAnn Thompson-Snipes, et al. *Interleukin-10: A Novel Stimulatory Factor for Mast Cells and Their Progenitors.* Journal of Experimental Medicine 173(2):507-510, Feb. 1991.
Daniel J. Capon, et al. *Designing CD4 immunoadhesins for Aids therapy.* Nature 337:525-531, Feb. 1989.
1995 Cytokine Research Products Catalog, Genzyme Diagnostics; Cambridge, MA (Portions thereof.).
R. Doug Wagner, et al. *Treatment with Anti-Interleukin-10 Monoclonal Antibody Enhances Early Resistance to but Impairs Complete Clearance of Listeria monocytogenes Infection in Mice*, Infection and Immunity 62(6):2345-2353, Jun. 1994.
Kenneth J. Pennlike, et al. *Recombinant Human IL-10 Prevents the Onset of Diabetes in the Nonobese Diabetic Mouse.* Clinical Immunology and Immunopathology 71(2):169-175, May 1994.

(Continued)

*Primary Examiner*—Prema Mertz
(74) *Attorney, Agent, or Firm*—Fish & Richardson P.C.

(57) ABSTRACT

Disclosed are chimeric proteins having a cytokine fused to an enzymatically inactive polypeptide which increases the circulating half-life of the cytokine. The chimeric proteins are useful for treating, inhibiting, or preventing a variety of conditions, including septic shock, granulomatous disorders, Type I diabetes, and various cancers (e.g., multiple myeloma) in a patient.

15 Claims, 10 Drawing Sheets

OTHER PUBLICATIONS

Nicholas F. Landolfi, et al. *A Chimeric IL-2/Il Molecule Possesses the Functional Activity of Both Proteins.* Journal of Immunology 146(3):915-919, Feb. 1991.

Alexander R. Duncan, et al. *The binding site for Clq and IgG* Nature 332:738-740, Apr. 1988.

Alexander R. Duncan, et al. *Localization of the binding site for the human high-affinity Fc receptor, on IgG.* Nature 332:563-564, Apr. 1988.

Xin Xiao Zheng, et al. *Administration of Noncytolytic IL-10/Fx in Murine Models of Lipopolysaccharide-Induced Septic Shock and Allogenic Islet Transplantation.* Journal of Immunology 154:5590-5600,1995.

Pedro O. Flores Villanueva, et al. *Role of IL-10 on Antigen-Presenting Cell Function for Schistosomal Egg-Specific Monoclonal T Helper Cell Responses in Vitro and in Vivo.* Journal of Immunology 151(6):3192-3198, Sep. 1993.

Summons to Attend Oral Proceedings Pursuant to Rule 71(1) EPC for Application European Application No. 95943058.8, filed Dec. 12, 1995.

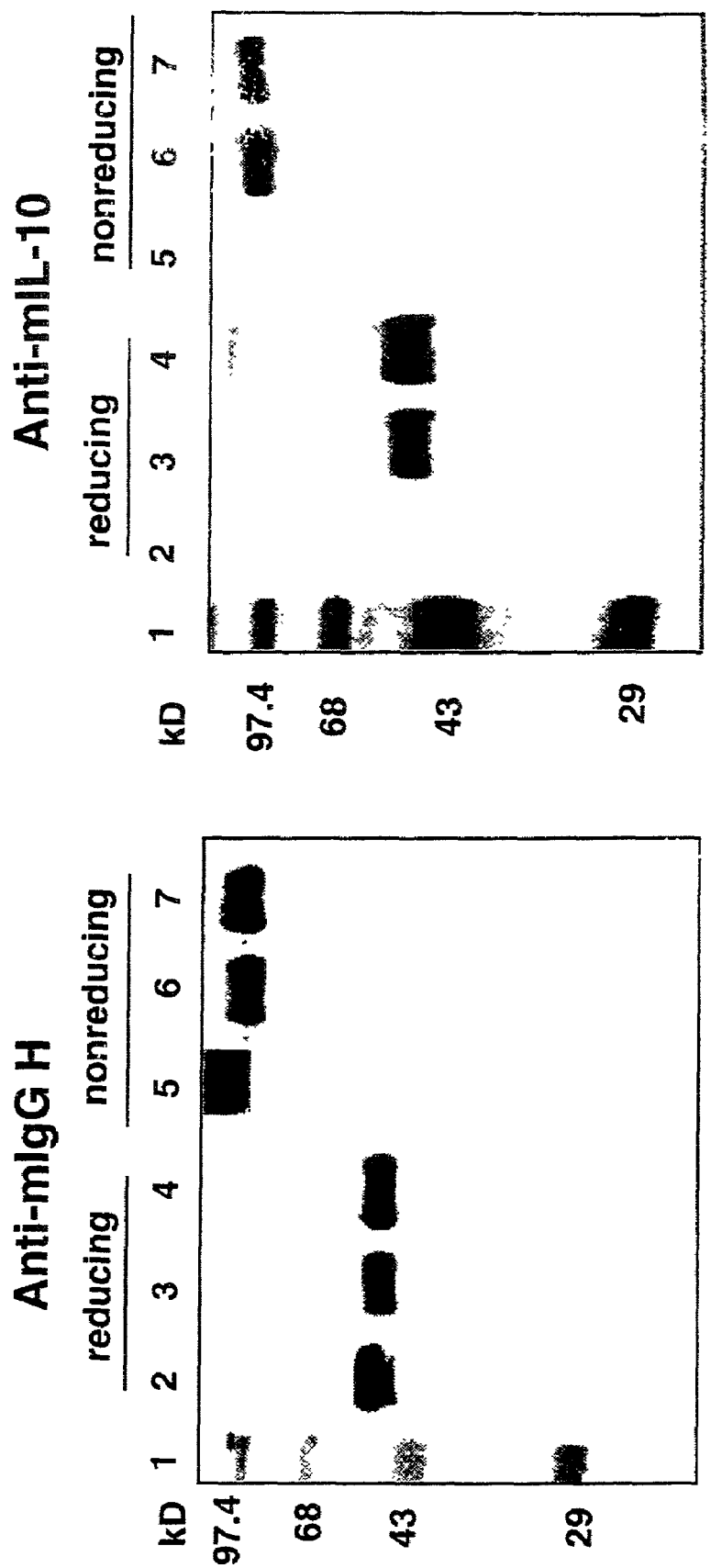

CHIMERIC IL-10

CROSS REFERENCE TO RELATED APPLICATION

This application is a Continuation of U.S. patent application 08/978,965, filed Nov. 6, 1997, now U.S. Pat. No. 6,403,077, which is a continuation in part of U.S. patent application Ser. No. 08/355,502, filed Dec. 12, 1994 now U.S. Pat. No. 6,410,008.

BACKGROUND OF THE INVENTION

This invention relates to chimeric proteins which include a cytokine and an enzymatically inactive polypeptide, and therapeutic uses thereof.

Cytokines have a wide range of effects on cell growth and differentiation. The value of certain cytokines has been recognized, including, for example, IL-2 for promoting the growth of activated T cells, B cells, LAK cells, and NK cells; IL-3 for promoting the growth of pluripotent hematopoietic progenitor cells; granulocyte macrophage-colony stimulating factor (GM-CSF) for promoting the growth and differentiation of neutrophils and macrophages, and for activating macrophages; kit ligand for promoting basophil and mast cell differentiation; IL-4 for promoting B cell proliferation, enhancing class II gene expression, enhancing IgG1 and IgE production, and promoting activated T cell proliferation and effector cell function; IL-5 for enhancing IgA production and stimulating eosinophil growth; IL-6 for transiently blocking myeloma growth, inducing immunoglobulin production, and inducing plasma cell and hepatocyte growth; IL-7 for inducing immature and mature B and T cell growth; and interferon-α and -β for their antiviral activity against papilloma viruses, hepatitis viruses, and herpes virus, and for treating hairy cell leukemia, myeloma, and other hematopoietic malignancies. Some additional functions of cytokines are summarized below.

Reported IL-1 activities include activation of T cells; induction of IL-2 receptor expression and cytokine gene expression; enhancement of collagenase, stromelysin, prostaglandin, and PDGF-AA synthesis by fibroblasts; co-stimulation of thymocyte proliferation; stimulation of pre-B cell differentiation; co-stimulation of B cell proliferation and Ig secretion; augmentation of IL-2 and IFN-induced activation of NK-mediated cytotoxicity; induction of adhesion molecule expression by endothelial cells; osteoblast and endothelial cell activation; enhancement of collagen production by epidermal cells; modulation of reparative functions following tissue injury; induction of insulin secretion; and β-islet cell cytotoxicity.

IL-1 has also been shown to stimulate the release of factors associated with the growth and differentiation of cells from myeloid and lymphoid lineages in vitro. IL-1 is thought to induce the production of granulocyte colony stimulating factor (G-CSF) and macrophage colony stimulating factor (M-CSF) by human marrow stromal cells; induce the production of GM-CSF and G-CSF by human dermal fibroblasts; and induce the production of GM-CSF by human peripheral blood lymphocytes. IL-1 also stimulates hematopoiesis by up-regulating receptors for colony stimulating factors and inducing the proliferation of pluripotent progenitors in the bone marrow. IL-1 has been shown to protect mice from otherwise lethal doses of radiation which indicates that this protein is useful in cancer therapy. Also, IL-1 has been shown to accelerate wound healing, presumably due to its ability to induce angiogenesis and fibroblast activation.

IL-2 has been reported to participate in the activation, tumoricidal activity, and growth of T cells, NK cells, and LAK cells; augment B cell growth and immunoglobulin production; augment IFN-γ production; induce IL-6 production by human monocytes; modulate histamine release by stimulated basophils; and modulate expression of the IL-2 receptor. Applications of IL-2 include anti-tumor therapy employing IL-2-activated LAK and TIL cell infusions; augmentation of IL-2 levels in treating immunodeficiency disorders, and increasing NK cell activity following bone marrow transplant.

Reported functions of IL-3 include stimulating the proliferation of mast cell lines; stimulating the formation of neutrophils, macrophages, megakaryocytes, basophils, eosinophils, and mast cells from isolated hematopoietic progenitors; enhancing growth of certain human T lymphocytes; and potentiating the activity of eosinophils, basophils, and monocytes. It has been shown that IL-3 exerts its ability to support multi-lineage colony formation early in the development of multipotent progenitors. IL-3 exhibits synergy with Stem Cell Factor (kit ligand) in inducing human $CD34^+$ cells to form basophils and mast cells. IL-3 has been used successfully in combination with factors such as GM-CSF to stimulate hematopoiesis in primates. In addition, sequential administration of IL-3 and IL-6 in primates stimulates thrombopoiesis. In vitro studies suggest that IL-3 can be used to reverse the hematopoietic toxicity associated with AZT treatment. Recombinant IL-3 has also been used in clinical trials in combination with other colony stimulating factors as a treatment for a plastic anemia.

IL-4 has been reported to be useful for up-regulating MHC Class II expression in resting B cells; enhancing IgG1, IgE, and sIgM production by B cells; up-regulating Fc receptor expression for IgE on B cells and monocytes; increasing viability and growth of normal resting T cells and certain T cell lines; co-stimulating growth in certain mast cell lines; maintaining $Lyt-2^-/L3T4^-$ thymic stem cells; promoting thymocyte maturation; enhancing the proliferation of granulocyte-macrophage progenitors, erythrocyte progenitors, and megakaryocytes in response to G-CSF, EPO, and IL-1, respectively; inhibiting human breast carcinoma cell growth in culture; inducing progression in B cells; inducing tumoricidal activity in cultured macrophages; and regulating adhesion molecule expression on endothelial cells.

Additionally, IL-4 is thought to act in combination with IL-1 as an autocrine growth factor for antigen-specific T cells to enhance antigen presentation and phagocytosis in macrophages. IL-4 not only enhances the development of cytotoxic T lymphocytes (CTL) from resting murine cells, but it also induces LAK activity. As a multifunctional cytokine that is reported to augment certain T and B cell responses, the therapeutic functions of IL-4 include reconstitution of cellular and humoral immune function following bone marrow transplantation; induction of terminal differentiation of acute lymphoblastoid leukemias; amelioration of immunodeficiency associated with hyper IgM; inhibition of the growth of solid tumors and B cell lymphomas; and reduction of inflammatory processes through down-regulation of production of IL-1, TNF, and IL-6. IL-4 has also been used in preclinical models to treat T cell-dependent autoimmune diseases, e.g., autoimmune diabetes mellitus and experimental and T cell-dependent allergic encephalomyelitis (Rapoport et al., 1993, J. Exp. Med. 178:87–99 and Racke et al., 1994, J. Exp. Med. 180:1961). Hence, IL-4 may be used in treating a variety of pathologies involving T cell-dependent immune-activities.

IL-5 has been shown to induce eosinophil colonies in human liquid bone marrow cultures to induce antibody-mediated killing of tumor cells by peripheral blood eosinophils. IL-5 also has been shown to stimulate murine B cells to differentiate and proliferate and to simulate IgA and IgM secretion in B cells. IL-5 is useful for treating pathologies related to alterations in eosinophil activity. For example, suggested uses of IL-5 include treatment of schistosomiasis (see, e.g., Sanderson, April 1989, "International Conference on the Clinical Impact of Interleukins" at the Royal College of Physicians in London). Other reports suggest the use of IL-5 in treating patients having certain tumors (see, e.g., Kolb et al., 1979, Br. J. Cancer 40:410; Pretlow et al., 1983, Cancer Res. 43:2997; and Iwasaki et al., 1986, Cancer 58:1321).

IL-6 is reported to exhibit multiple functions, including induction of proliferation in a number of cells, including EBV-transformed B cells, T cells, mesangial cells, and keratinocytes; enhancement of the IL-3-dependent proliferation of multipotential hematopoietic progenitors; promotion of megakaryocyte maturation; triggering of neuronal differentiation; growth inhibition of certain melanoma cell lines, myeloid leukemic cell lines, and breast carcinoma cell lines; induction of B cell differentiation; stimulation of IgG secretion; and induction of cytotoxic T cell differentiation.

Additionally, IL-6 acts on murine thymocytes to induce the differentiation of Lyt-2$^+$ CTL in the presence of IL-2, and IL-6 supports the proliferation of Con-A or T cell receptor antibody-stimulated T cells in vitro. IL-6 has also been reported to co-stimulate thymocyte proliferation and induce the release of acute phase reactants from hepatocytes. IL-6 is also thought to be an autocrine growth factor for tumor cells from patients with multiple myeloma.

IL-7 has been reported to have T cell growth factor activity. Stem cell factor synergizes with IL-7 to stimulate proliferation of early T cell progenitors. Also, IL-7 acts as a co-stimulus with Con A to induce the proliferation of purified murine T cells. IL-7 has also been reported to induce proliferation of human peripheral blood T lymphocytes in the presence of sub-mitogenic doses of Con A and PHA. Certain studies suggest that IL-7 acts directly on human CD8$^+$ T cells to augment cytotoxicity and that IL-7 is a potent differentiation factor for the development of CTL.

In mice, IL-7 has been shown to act on CD8$^+$ T cells to induce CTL in an IL-2- and IL-6-dependent manner. IL-7 is required for the IL-1-induced proliferation of murine thymocytes. IL-7 has further been shown to induce LAK activity from CD8$^+$ cells prepared from murine peripheral lymphoid tissues. IL-7 has been shown to increase surface expression of the ICAM-1 molecule on melanocytes and melanoma cells. Injection of IL-7 into mice leads to a 3- to 5-fold increase in circulating immature B cells with a concurrent 90% reduction in myeloid progenitors in the bone marrow and a 15-fold increase in myeloid progenitors in the spleen. Hence, IL-7 is thought to have a similar spectrum of therapeutic activities in vivo as those reported for IL-2.

IL-9 stimulates the proliferation of mouse erythroid progenitors and promotes erythroid differentiation of cells in the presence of erythropoietin and IL-3 (Bourett et al., 1992, Exp. Hematol. 20:868). IL-9 has also been shown to enhance the survival of T cell lines in vitro (Renaud et al., 1990, Cytokine 2:9). IL-9 also potentiates IL-4-dependent Ig production by human B lymphocytes, and it promotes IL-6 production by murine mast cells lines derived from bone marrow. In addition, IL-9 is involved in the differentiation of hippocampal progenitors (Uyttenhove et al., 1991, J. Exp. Med. 173:519).

IL-10 is a cytokine produced by activated Th2 cells, B cells, keratinocytes, monocytes, and macrophages (Moore et al., 1993, Annu. Rev. Immunol. 11:165). IL-10 can be used to stimulate growth and differentiation of activated human B cells. In vitro, murine and human IL-10 inhibit cytokine synthesis (e.g., IFN-γ, TNF-β, and IL-2) by Th1 cells, NK cells, monocytes, and macrophages (Fiorentino et al., 1989, J. Exp. Med., 170:2081–2095; Fiorentino et al., 1991, J. Immunol. 146:3444; Hsu et al., 1992, Int. Immunol. 4:563; Hsu et al., 1992, Int. Immunol. 4:563; D'Andrea et al., 1993, J. Exp. Med. 178:1041; and de Waal Malefyt et al., 1991, J. Exp. Med. 174:915; Fiorentino et al., 1991, J. Immunol. 147:3815). Thus IL-10 is useful for inhibiting Th1 responses to prevent transplant rejection and T cell-mediated autoimmune diseases, such as type I diabetes and multiple sclerosis. The ability of IL-10 to inhibit secretion of the pro-inflammatory cytokines (e.g., IL-1, IL-6, IL-8, and TNF-α) suggests that IL-10 is a useful anti-inflammatory agent in the treatment of rheumatoid arthritis and psoriasis.

IL-10 has been recognized for its value in treating septicemia. Gram-negative septicemia in hospitalized patients is invariably associated with high morbidity and mortality (Bone, 1991, Ann. Intern. Med. 115:457). Case fatality rates of 20–60% reflect the frequent development of acute lung injury (Byrne et al., 1987, Acute Care 13:206) and multiple organ failure (Abrams et al., 1989, Surg. Rounds 12:44), as well as the lack of effective therapies. Endotoxin (LPS), a product of gram-negative bacteria, is a major causative agent in the pathogenesis of septic shock (Glausner et al., 1991, Lancet 338:732). A septic shock-like syndrome can be induced experimentally by a single injection of LPS into animals. Injection of IL-10 into mice inhibits secretion of tumor necrosis factor in vivo and protects against the lethal effects of endotoxin (Gerard et al., 1993, J. Exp. Med. 177(2):547; de Waal Malefyt et al., 1991, J. Exp. Med. 174:915; Fiorentino et al., 1991, J. Immunol. 147:3815; and Moore et al., 1990, Science 248:1230).

Upon infection with Schistosoma, a genus of flatworms, the organism deposits its eggs into the liver, causing granuloma formation and fibrosis of liver tissue. Liver damage caused by Schistosome infection can lead to cirrhosis of the liver. Schistosomiasis is often chronic and debilitating.

Naturally-occurring cytokines have short circulating half-lives; for example, naturally-occurring IL-10 is therapeutically effective for approximately 30 minutes following administration (Gerard et al., 1993, J. Exp. Med. 177(2):547).

SUMMARY OF THE INVENTION

I have discovered that the in vivo half-life of a cytokine can be increased by bonding the cytokine to a polypeptide which increases the longevity of the cytokine while being enzymatically inactive in humans, and I have discovered that certain of the chimeric cytokines (i.e., chimeric proteins or chimeras) are useful for treating or inhibiting the onset of conditions such as septic shock, granulomatous disorders (e.g., schistosomiasis), Type I diabetes, certain cancers (e.g., multiple myeloma), and chronic infections.

Accordingly, in one aspect, the invention features a chimeric protein having a cytokine bonded to a polypeptide which is enzymatically inactive in humans and which increases the circulating half-life of the cytokine in vivo by a factor of at least 2, and preferably by a factor of at least 10.

Useful enzymatically inactive pglypeptides include not only proteins that are not enzymes, such as albumin, but also enzymes that have enzymatic activity in an organism other than humans but which are inactive in humans. For example, useful polypeptides include plant enzymes, porcine or rodent glycosyltransferases, and α-1,3-galactosyltransferases (see, e.g., Sandrin et al., 1993, PNAS 90:11391).

The enzymatically inactive polypeptide can include an IgG hinge region and a half-life increasing polypeptide. In this embodiment, the IgG hinge region is bonded to the cytokine and serves as a flexible polypeptide spacer between the cytokine and the half-life-increasing polypeptide (e.g., IgG Fc or albumin).

When the enzymatically inactive polypeptide includes an IgG hinge region and the Fc region of an IgG molecule, it lacks an IgG variable region of a heavy chain so that the binding specificity conferred by the variable region is lacking in the chimera. The Fc region can include a mutation which inhibits complement fixation and prevents Fc from binding the Fc receptor with high affinity, thus preventing the chimera from being lytic. Alternatively, the Fc region can be lytic, i.e., be able to bind complement and bring about lysis of the cell to which the chimera binds.

The cytokine portion of the chimeric protein can be an interleukin, such as IL-10, IL-6, IL-4, IL-1, IL-2, IL-3, IL-5, IL-7, IL-8, IL-9, IL-12, or IL-15. Other useful cytokines include GM-CSF, G-CSF, interferons (e.g., IFN-α, IFN-β, and IFN-γ), and tumor necrosis factors (e.g., TNF-α and TNF-β).

A chimeric cytokine of the invention can be used in a therapeutic composition formed by admixture of the chimeric protein with a pharmaceutically acceptable carrier. In various embodiments, the invention provides methods for treating or inhibiting the development of a variety of conditions. For example, the IL-10 chimeras and IL-4 chimeras can each be used to treat or inhibit granuloma formation (e.g., schistosomiasis). IL-10 chimeras and IL-4 chimeras are also useful for inhibiting the development of Type I diabetes, for treating or inhibiting the development of Crohn's disease, ulcerative colitis, or Boeck's disease. The IL-10 chimera is useful for treating or inhibiting septic shock. IL-6 chimeras are useful for treating or inhibiting the development of multiple myelpma in a patient. TNF-α chimeras and TNF-β chimeras each are useful for combatting cervical cancer caused by papilloma viruses, liver cancer caused by hepatitis viruses, and skin eruptions caused by herpes viruses.

By "cytokine" is meant any of the non-antibody proteins released by one cell population (e.g., primed T-lymphocytes) on contact with specific antigen, which act as intercellular mediators, as in the generation of an immune response. One important class of cytokines are those which induce proliferation of lymphocytes, e.g., T cells.

By IgG "Fc" region is meant a naturally-occurring or synthetic polypeptide homologous to the IgG C-terminal domain that is produced upon papain digestion of IgG. IgG Fc has a molecular weight of approximately 50 kD. In the molecules of the invention, the entire Fc region can be used, or only a half-life enhancing portion. In addition, many modifications in amino acid sequence are acceptable, as native activity is not in all cases necessary or desired.

By "non-lytic" IgG Fc is meant an IgG Fc region which lacks a high affinity Fc receptor binding site and which lacks a C'1q binding site. The high affinity Fc receptor binding site includes the Leu residue at position 235 of IgG Fc; the Fc receptor binding site can be functionally destroyed by mutating or deleting Leu 235. For example, substitution of Glu for Leu 235 inhibits the ability of the Fc region to bind the high affinity Fc receptor. The C'1q binding site can be functionally destroyed by mutating or deleting the Glu 318, Lys 320, and Lys 322 residues of IgG1. For example, substitution of Ala residues for Glu 318, Lys 320, and Lys 322 renders IgG1 Fc unable to direct ADCC.

By "lytic" IgG Fc is meant an IgG Fc region which has a high affinity Fc receptor binding site and a C'1q binding site. The high affinity Fc receptor binding site includes the Leu residue at position 235 of the IgG Fc. The C'1q binding site includes the Glu 318, Lys 320, and Lys 322 residues of IgG1. Lytic IgG Fc has wild-type residues or conservative amino acid substitutions at these binding sites. Lytic IgG Fc can target cells for antibody dependent cellular cytotoxicity (ADCC) or complement directed cytolysis (CDC).

By IgG "hinge" region is meant a polypeptide homologous to the portion of a naturally-occurring IgG which includes the cysteine residues at which the disulfide bonds linking the two heavy chains of the immunoglobulin form. For IgG1, the hinge region also includes the cysteine residues at which the disulfide bonds linking the γ1 and light chains form. The hinge region is approximately 13–18 amino acids in length in IgG1, IgG2, and IGg4; in IgG3, the hinge region is approximately 65 amino acids in length.

By polypeptide "spacer" is meant a polypeptide which, when placed between the half-life-increasing polypeptide and a cytokine, possesses an amino acid residue with a normalized B value ($B_{norm}$; a measure of flexibility) of 1.000 or greater, preferably of 1.125 or greater, and, most preferably of 1.135 or greater (see, e.g., Karplus et al., 1985, Naturwissenschaften 72:212). Amino acids which are commonly known to be flexible include glutamic acid, glutamine, threonine, lysine, serine, glycine, proline, aspartic acid, asparagine, and arginine.

The invention offers several features and advantages: (1) the chimeric proteins of the invention have an extended circulating half-life and provide long term protection; (2) because many of the cytokines and longevity-increasing polypeptides useful in the invention have already been purified, the chimeric proteins can easily be purified by employing methods that have been described for purifying the cytokine or longevity-increasing polypeptide; (3) some of the chimeric proteins are mutated such that they are defective for antibody-dependent cell-mediated cytotoxicity (ADCC) and complement directed cytolysis (CDC), thus making them useful for treating or inhibiting the onset of septic shock, type I diabetes, or multiple myeloma without destroying the target cells.

An additional advantage of chimeric proteins that include an Fc polypeptide is that they cannot cross the blood/brain barrier and enter the brain where polypeptides such as IL-6, tumor necrosis factor, IL-1α, and IL-1β could cause side effects by reacting with regulatory centers in the brain. Among the side effects caused by these cytokines in the absence of an Fc polypeptide are somnolence, fever, and hypotension.

Other features and advantages of the invention will be apparent from the following description of the preferred embodiments thereof, and from the claims.

DETAILED DESCRIPTION

The drawings will first be briefly described.

DRAWINGS

FIG. 1 is a schematic representation of the scheme used for the genetic fusion of murine IL-10 and murine Fcγ2a cDNAs to create a murine IL-10/Fc chimeric cytokine.

Mutations were made in the CH2 domain of a Fcγ2a fragment with site-directed mutagenesis to replace Glu 318, Lys 320, and Lys 322 with Ala residues; Leu 235 was replaced with Glu to render the IL-10/Fc chimeric protein ineffective in directing ADCC and CDC. The non-lytic chimeric protein is referred to hereinafter as "IL-10/Fc." The lytic chimeric protein (without the mutation) is referred to as "IL-10/Fc++."

FIGS. 2A–B are reproductions of blots obtained by Western blot analysis of the IL-10/Fc chimeric protein. The SDS-polyacrylamide gels were run under reducing (lanes 2–4) and non-reducing (lanes 5–7) conditions. Western blotting was performed with antibodies directed against mIgG Fc (FIG. 2A), or mIL-10 (FIG. 2B). For both FIG. 2A and FIG. 2B, lane 1 was loaded with a high molecular weight protein standard; lanes 2 and 5 were loaded with mIgG2a; lanes 3 and 6 were loaded with IL-10/Fc++; and lanes 4 and 7 were loaded with IL-10/Fc.

FIG. 3 is a histogram demonstrating that rIL-10 (wild-type, recombinant IL-10) and IL-10/Fc inhibit LPS-induced production of IL-6 by macrophages. PU5-1.8 cells ($10^6$ cells/ml) were pre-incubated with various concentrations of IL-10/Fc or rIL-10, as indicated, for 24 hours. LPS (10 μg/ml) then was added, and the cells were incubated for an additional 24 hours. Supernatants were collected and the IL-6 concentration was assayed by ELISA.

FIG. 4 is a histogram showing the co-stimulatory effects of IL-10/Fc on mast cell proliferation. The ability of rIL-10 or IL-10/Fc to enhance IL-4-dependent growth of MC/9 mast cells was assessed in a [$^3$H] thymidine incorporation assay. MC/9 mast cells ($5\times10^3$ cells/ml) were cultured for 3 days with rIL-10 (100 U/ml), IL-10/Fc (100 U/ml), rIL-4 (100 U/ml), or combinations of these factors in the presence or absence of a neutralizing anti-murine IL-10 mAb as indicated.

FIG. 5 is a plot of the IL-10/Fc circulating half-life. The time-related serum concentration of IL-10/Fc was determined following a single bolus intravenous dose (8 μg) of the chimeric protein. Blood samples were obtained by retro-orbital bleeding at the indicated intervals. IL-10/Fc levels were detected by ELISA with a rat-anti-mouse IL-10 mAb as the capture antibody and horseradish peroxide-conjugated rat anti-mouse IgG heavy chain mAb as the detection antibody.

FIG. 6 is a series of FACS profiles indicating that, as is desired, IL-10/Fc exhibits poor FcγR I binding activity. FcγR I binding assays were performed using human FcγR I cDNA transfected CHO cells (murine FcγR I, FcγR II, and IL-10 receptor negative). The FcγR I binding ability of IL-10/Fc++ and IL-10/Fc was analyzed by FACS.

FIG. 7 is a plot showing that IL-10/Fc confers prolonged protection from the lethal effects of LPS following an injection of 500 μg LPS. This plot shows the survival rates for the following six groups of BALB/c mice: (i) 12 mice which were treated for 30 minutes with rIL-10; (ii) 12 mice which were treated for 30 minutes with 2,000 U of IL-10/Fc; (iii) 12 mice which were treated for 24 hours with 4,000 U of IL-10/Fc; (iv) 12 mice which were treated for 30 minutes with phosphate buffered saline; (v) 6 mice which were treated for 30 minutes with 0.6 μg mIgG2a; and (vi) 12 mice which were treated for 24 hours with 4,000 U rIL-10.

Figure 12:
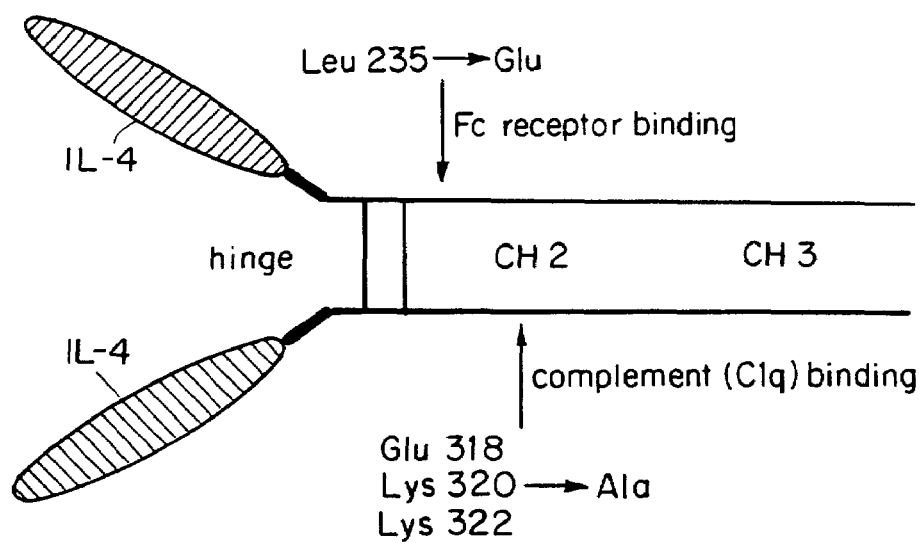

FIG. 12 is a schematic representation of the scheme used for the genetic fusion of murine IL-4 and murine Fcγ2a cDNAs to create a non-lytic murine IL-4/Fc chimeric cytokine. Mutations were made in the CH2 domain of a Fcγ2a fragment with site-directed mutagenesis to replace Glu 318, Lys 320, and Lys 322 with Ala residues; Leu 235 was replaced with Glu to render the IL-4/Fc chimeric protein ineffective in directing ADCC and CDC. The non-lytic chimeric protein is referred to hereinafter as "IL-4/Fc." The lytic chimeric protein (without the mutation) is referred to as "IL-4/ Fc++."

Figure 13:
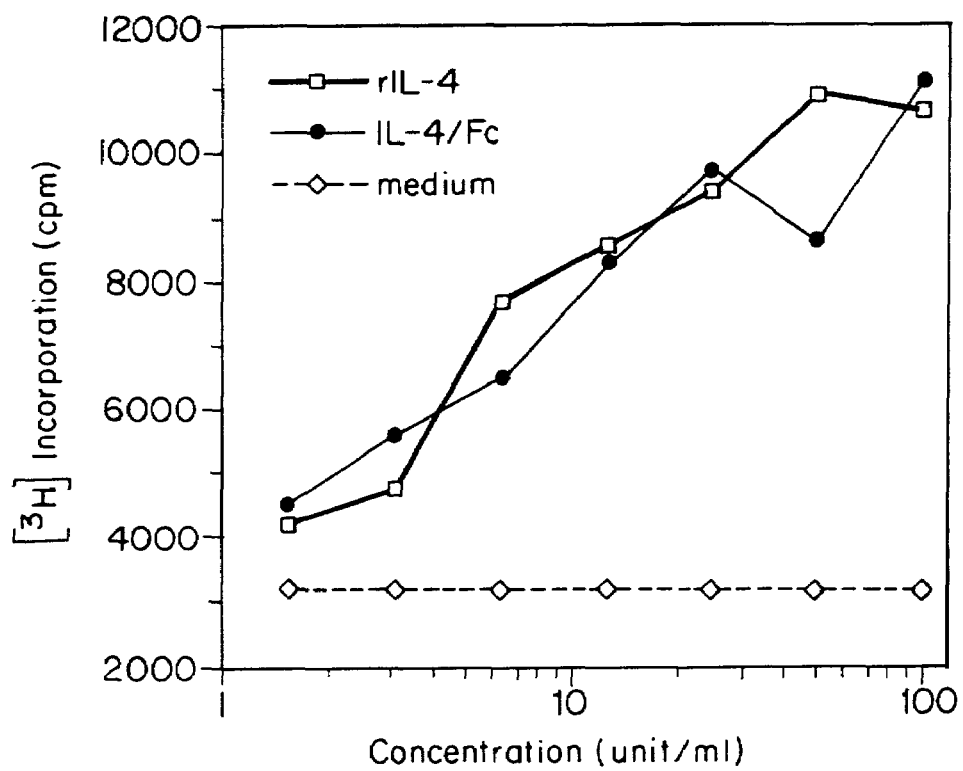

FIG. 13 is a plot of the $^3$H incorporated into cells in a CTLL-2 proliferation assay versus the concentration of recombinant IL-4or IL-4/Fc in the assay. Recombinant IL-4 and IL-4/Fc were used at equivalent molar concentrations of IL-4, as determined by ELISA.

Figure 14:
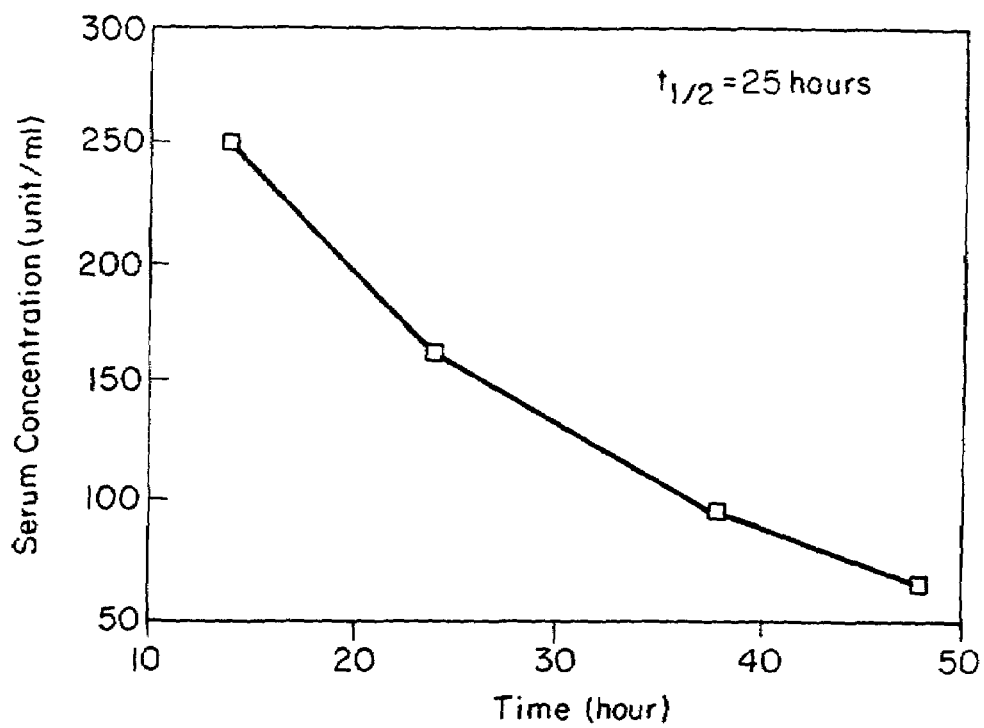

FIG. 14 is a graph which indicates that the circulating half-life of non-lytic IL-4/Fc is 25 hours.

Figure 15:
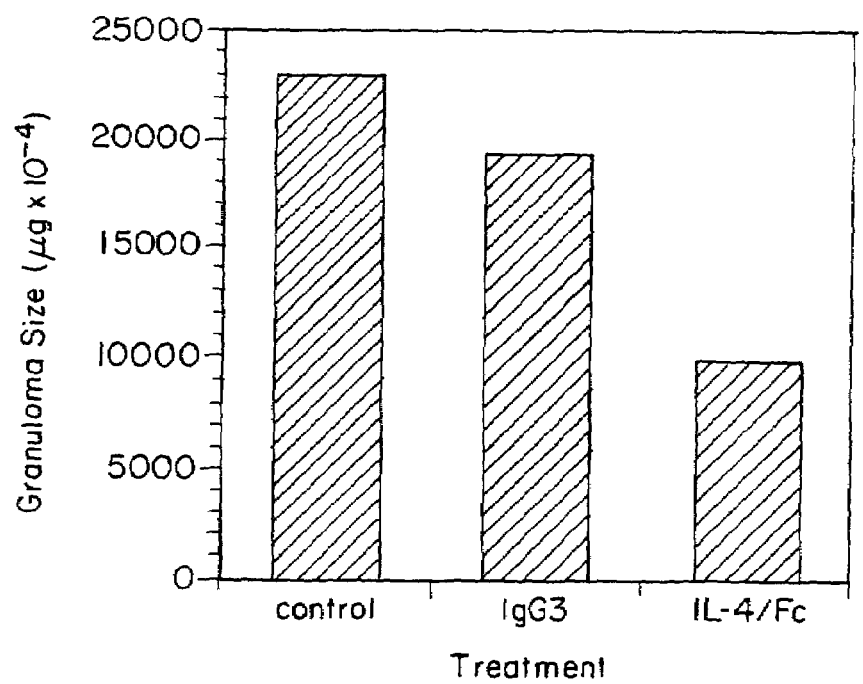

FIG. 15 is a histogram showing that non-lytic IL-4/ Fc down-regulates granuloma size in livers of Schistosome-infected mice.

ABBREVIATIONS

The following abbreviations are used herein:

| | |
|---|---|
| ADCC | antibody dependent cell-mediated cytotoxicity |
| CDC | complement directed cytolysis |
| CMV | cytomegalovirus |
| Con A | concanavalin A |
| GM-CSF | granulocyte macrophage-colony stimulating factor |
| HBSS | Hank's balanced salt solution |
| IL | interleukin |
| NOD | non-obese diabetic |
| PBS | phosphate-buffered saline |
| TNF | tumor necrosis factor |

Before providing detailed working examples of the invention, I have described some of the parameters of the invention.

Chimeric Cytokines: Conventional molecular biology techniques can be used to produce chimeric proteins having a cytokine (e.g., an interleukin) bonded to an enzymatically inactive polypeptide (e.g., a lytic or non-lytic Fc region of IgG). Numerous polypeptides are suitable for use as enzymatically inactive proteins in the invention. Preferably, the protein has a molecular weight of at least 10 kD; a net neutral charge at pH 6.8; a globular tertiary structure; human origin; and no ability to bind to surface receptors other than a receptor for the cytokine (e.g., the IL-10 receptor). Where the enzymatically inactive polypeptide is IgG, preferably, the IgG portion is glycosylated. If desired, the enzymatically inactive polypeptide can include an IgG hinge region positioned such that the chimeric protein has a cytokine bonded to an IgG hinge region with the hinge region bonded to a longevity-increasing polypeptide. Thus, the hinge region can serve as a spacer between the cytokine and the longevity-increasing polypeptide. A person skilled in molecular biology can readily produce such molecules from an IgG2a-secreting hybridoma (e.g., HB129) or other eukaryotic cells or baculovirus systems. As an alternative to using an IgG hinge region, a flexible polypeptide spacer, as defined herein, can be used. Using conventional molecular biology techniques, such a polypeptide can be inserted between the cytokine and the longevity-increasing polypeptide.

Where the enzymatically inactive protein includes an Fc region, the Fc region can be mutated, if desired, to inhibit its ability to fix complement and bind the Fc receptor with high affinity. For murine IgG Fc, substitution of Ala residues for Glu 318, Lys 320, and Lys 322 renders the protein unable to direct ADCC. Substitution of Glu for Leu 235 inhibits the ability of the protein to bind the Fc receptor with high affinity. Appropriate mutations for human IgG also are known (see, e.g., Morrison et al., 1994, The Immunologist 2: 119–124 and Brekke et al., 1994, The Immunologist 2: 125). Other mutations can also be used to inhibit these activities of the protein, and art-recognized methods can be used to assay for the ability of the protein to fix complement or bind the Fc receptor. Other useful enzymatically inactive polypeptides include albumin (e.g., human serum albumin), transferrin, enzymes such as t-PA which have been inactivated by mutations, and other proteins with a long circulating half-life and without enzymatic activity in humans.

Numerous cytokines have been cloned and are useful in the invention. Conventional methods can readily be used to subclone a gene encoding a desired cytokine into a vector for production a chimeric protein. For example, the murine IL-10 gene has been described (Moore et al., 1990, Science 248: 1230–1234), and the human IL-10 gene has been cloned (see, e.g., U.S. Pat. Ser. No. 5,231,012, incorporated herein by reference). Human IL-4 has also been cloned (Yokata et al., 1986, PNAS 83:5894). If desired, the cytokine can be truncated or mutated as long as it retains a useful biological function, as determined with conventional methods for assaying cytokine function.

Preferably, the enzymatically inactive polypeptide used in the production of the chimeric protein (e.g., IgG Fc) has, by itself, an in vivo circulating half-life greater than that of the cytokine (e.g., IL-10). More preferably, the half-life of the chimeric protein is at least 2 times that of the cytokine alone. Most preferably, the half-life of the chimeric protein is at least 10 times that of the cytokine alone. The circulating half-life pf the chimeric protein can be measured in an ELISA of a sample of serum obtained from a patient treated with the chimeric protein. In such an ELISA, antibodies directed against the cytokine can be used as the capture antibodies, and antibodies directed against the enzymatically inactive protein can be used as the detection antibodies, allowing detection of only the chimeric protein in a sample. Conventional methods for performing ELISAs can be used, and a detailed example of such an ELISA is provided herein.

The chimeric proteins can be synthesized (e.g., in mammalian cells) using conventional methods for protein expression using recombinant DNA technology. Because many of the polypeptides used to create the chimeric proteins have been previously purified, many of the previously-described methods of protein purification should be useful, along with other conventional methods, for purifying the chimeric proteins of the invention. If desired, the chimeric protein can be affinity-purified according to standard protocols with antibodies directed against the cytokine. Antibodies directed against the enzymatically inactive protein are also useful for purifying the chimeric protein by conventional immunoaffinity techniques. If desired, the activity of the chimeric protein can be assayed with methods that are commonly used to test the activity of the cytokine alone. It is not necessary that the activity of the chimeric cytokine be identical to the activity of the cytokine alone. For example, the chimeric cytokine may be more or less active than is the cytokine alone.

Therapeutic Use of Chimeric Cytokines:

The chimeric cytokines of the invention can be used to treat or inhibit (including completely preventing) the onset of a variety of conditions in a patient, including septicemia, septic shock, granuloma formation, Type I diabetes, multiple myeloma, bacterial or fungal infections, virus-associated cancers (e.g., Burkitt's lymphoma), and certain other cancers. The therapeutic uses of the chimeric cytokines are correlated with the therapeutic uses of the cytokines in the absence of the enzymatically inactive half-life-increasing polypeptide. Thus, the chimeric cytokines of the invention can substitute for their corresponding cytokines in numerous previously described applications, such as those which are summarized herein.

Where the. cytokine is IL-10, a therapeutic composition that includes an IL-10 chimera can be administered to a patient to treat or inhibit septicemia or septic shock. Where the cytokine is IL-10 or IL-4, the chimeric cytokine can be used to treat or inhibit granulomatous disorders (e.g., schistosomiasis), Crohn's disease (i.e., regional enteritis), multiple sclerosis, psoriasis, rheumatoid arthritis, systemic lupus erythematosus, iritis, inflammatory bowel disease, and Boeck's disease (sarcoidosis). IL-5 chimeras can be used to treat granulomatous disorders such as schistosomiasis, and IL-5 chimeras can be used to induce antibody-mediated killing of tumor cells by peripheral blood eosinophils. These chimeras are also useful for enhancing IgA production and stimulating eosinophil growth. Where the cytokine is IL-6, the chimeric cytokine is particularly useful for treating multiple myelomas, breast carcinomas, and melanomas; and inducing neuronal, cytotoxic T cell, and B cell differentiation. IL-6 chimeras are also useful for their anti-viral activity, and for inducing hybridoma and hepatocyte growth. Chimeric cytokines that include a tumor necrosis factor (e.g., TNF-α or TNF-β) are useful for treating or inhibiting cervical cancers that are associated with papilloma virus infections, liver cancers that are associated with hepatitis virus infections, and skin eruptions that are associated with herpes virus infections.

IL-1, IL-2, IL-3, IL-6, and IL-15 can be used as growth factors for hematological deficiencies, and they are useful protecting against side effects, or facilitating recovery, in irradiation therapy or chemotherapy. Other examples of the functions of the chimeric proteins include IL-2 or IL-15 chimeras for promoting the growth of activated T cells, B cells, LAK cells, and NK cells. IL-3 chimeras are useful for promoting the growth of pluripotent hematopoietic progenitor cells and reversing the hematopoietic toxicity associated with AZT treatment. IL-3 chimeras can also be used to treat a plastic anemia. GM-CSF chimeras are useful for promoting the growth and differentiation of neutrophils and macrophages, and for activating macrophages. Other chimeric cytokine activities include IL-7 chimeras for inducing immature B and T cell growth.

Where the Fc region of the chimeric protein is lytic, the chimeric protein is particularly useful for treating multiple myeloma. Lytic Fc chimeras can be used to deplete the patient of suppressor lymphocytes and to suppress chronic immunity. Lytic Fc chimeras can also be used to treat cancers, such as those which are associated with viruses. For example, lytic Fc chimeras of the invention can be used to treat renal cell carcinomas, melanomas, lymphomas, Papilloma virus-associated cervical cancers, or Kaposi's sarcoma. In addition, the invention can be used to combat liver cancer caused by infections with hepatitis B or hepatitis C. The invention is also useful for treating Epstein Barr Virus-associated lymphomas, such as Burkitt's lymphoma.

Chimeric cytokines that include a lytic Fc can also be used to treat chronic infections, such as infections associated with suppression of the immune system, e.g., Acquired Immune Deficiency Syndrome (AIDS)-associated infections. Examples of AIDS-associated infections that are commonly seen include infections with protozoa (e.g., *Pneumocystis carinii, Toxoplasma gondii*, and *Cryptosporidium*), fungi (e.g., *Candida sp.* and *Cryptococcus neoformans*), viruses (e.g., Cytomegalovirus, *Herpes simplex*, and *Herpes zoster*), or bacteria (e.g., *Mycobacterium avium-intracellulare* and *Mycobacterium tuberculosis*). Such infections can cause pneumonia, impairment of the central nervous system, diarrhea, esophagitis, meningitis, retinitis, or colitis.

The invention can also be used to treat non-AIDS-associated infections with various species of mycobacteria. These bacteria are causative agents in the etiology of a number of conditions. For example, *M. tuberculosis* infections cause tuberculosis; *M. abscessus* cause a traumatic infection of the knee; *M. bovis* is the primary cause of tuberculosis in cattle and is transmissible to humans and other animals; *M. intracellulare* is associated with lung lesions in humans; *M. kansasii* causes a tuberculosis-like pulmonary disease and causes infections, and usually lesions, in the spleen, liver, pancreas, testes, joints, and the lymph nodes; *M. leprae* causes leprosy; *M. scrofulaceum* is associated with inflammation of the cervix in children, and lesions in leprosy patients; and *M. ulcerans* causes Buruli ulcers in humans.

The invention can also be used to treat leishmaniasis, including acute and diffuse cutaneous forms, mucocutaneous forms, and visceral forms. These infections, caused by species such as *L. major, L. tropica*, various strains of *L. mexicana, L. braziliensis*, and *L. donovani*, can result in lesions and ulcers over the body.

A therapeutic composition that includes a chimeric protein of the invention can be formulated, according to standard protocols, by admixture of the chimeric protein and a pharmaceutically acceptable carrier such as water or saline. If desired, a combination of chimeric proteins can be administered to a patient, either sequentially or simultaneously (e.g., treatment of granuloma formation by administration of IL-10/Fc, followed by administration of IL-4/albumin). The chimeric protein can be administered to a patient intravenously, intraperitoneally, intramuscularly, and/or subcutaneously. Generally, a chimeric protein dosage of 1 µg/kg body weight to 500 mg/kg body weight can be used; preferably, the dosage is 10 µg/kg body weight to 100 µg/kg body weight. Preferably, the chimeric protein is administered before or at the first sign of disease onset; if desired, the chimeric protein can be administered before signs of disease appear. Those skilled in the art of medicine will be able to adjust the dosage and frequency of administration as desired. Generally, the chimeric proteins will be administered at 12-hour intervals. The efficacy of the treatment can be determined by monitoring the patient for commonly-known signs of the disease, or by assaying fluid (e.g., serum) samples of the patient for the presence of the chimeric protein.

Inhibition of Septic Shock: Septic shock in a patient (e.g., a human) can be treated or inhibited by administering to the patient a therapeutically effective amount of a chimeric protein which has an IL-10 polypeptide bonded to an enzymatically inactive (in humans) polypeptide which increases the circulating half-life of the cytokine by a factor of at least 2. For example, a chimeric protein having an IL-10 polypeptide bonded to an Ig hinge region with the hinge region bonded to a lytic or non-lytic IgG Fc region can be used (these polypeptides are referred to herein as IL-10/Fc++ and IL-10/Fc, respectively). The chimeric protein can be formulated in a pharmaceutically acceptable carrier, e.g., saline, for administration (e.g., intravenous administration) to the patient. Generally, a dosage of 0.01 mg/kg to 500 mg/kg body weight is sufficient; preferably, the dosage is 10 µg/kg to 100 µg/kg. If desired, the efficacy of the treatment regimen can be assessed with conventional methods of monitoring patients for septic shock.

Treatment is begun with the diagnosis or suspicion of septicemia or endotoxemia, and treatment is repeated at 12-hour intervals until stabilization of the patient's condition is achieved. Such an assessment can be made on the basis of the observation that serum TNF levels are undetectable by ELISA. The patient's condition can also be monitored by measuring the level of the circulating chimeric protein at 4-hour intervals. The chimeric protein level can be measured using a two-point ELISA in which antibodies directed against the cytokine are used as the capture antibodies and antibodies directed against the enzymatically inactive protein are used as the detection antibodies.

Inhibition of the Development of Diabetes: The chimeric IL-10 and IL-4 molecules of the invention can each be administered to patients (e.g., humans) to treat or inhibit the development of diabetes. The chimeric protein can be formulated as a therapeutic composition by admixture of the chimeric protein with a pharmaceutically acceptable carrier (e.g., saline). Using conventional methods, such therapeutic compositions can be formulated for intraperitoneal, intravenous, subcutaneous, or intramuscular administration. Preferably the therapeutic composition is administered to the patient upon discovery of anti-beta cell autoimmunity and/or subtle pre-diabetic changes in glucose metabolism (i.e., blunted early i.v. glucose tolerance test), and administration is repeated every other day, or at a frequency of at least once per week. The preferred dosage of the chimeric protein can be determined by using standard techniques to monitor glucose levels, anti-beta cells autoantibody level, or abnormalities in glucose tolerance tests of the patient being treated. For humans, a chimeric protein dosage of 1 µg to 500 mg/kg body weight is sufficient. Generally, the preferred dosage is 1 to 200 µg/kg; more preferably, the dosage is approximately 50 µg/kg.

Treatment of Cancer: The lytic chimeric proteins of the invention are useful for treating a number of cancers, e.g., multiple myeloma, in a human. For example, naturally-occurring IL-10 is known to inhibit the production of IL-6 and tumor necrosis factor. Multiple myeloma is a malignant plasma cell disorder in which IL-6 functions as an autocrine growth factor for many of the cells involved. In addition, multiple myeloma cells bear IL-10 receptors, and thus the IL-10 portion of an IL-10/FC++ chimeric protein targets the protein to the cancer cells which are then lysed by the lytic Fc portion of the chimera. In this aspect of the invention, a therapeutic composition of a pharmaceutically acceptable carrier and a chimeric cytokine (e.g., IL-10/Fc++) is administered to a patient diagnosed with multiple myeloma. Similarly, other lytic chimeric cytokines can be used to treat cancers of cells bearing receptors for the cytokine portion of the chimera.

There now follow detailed working examples of the use of chimeric proteins of the invention to prevent (i.e., completely inhibit the development of) septic shock in a patient, to inhibit granuloma formation (e.g., schistosomiasis), and to prevent the onset of diabetes in a patient.

Treatment of Septic Shock with IL-10/Fc Genetic Construction of IL-10/Fc: Complementary DNAs for murine IL-10 and murine Fcγ2a were generated from mRNA extracted from concanavalin (Con A)-stimulated murine splenic cells (C57BL/6J; Jackson Laboratory, Bar Harbor, Me.) and an IgG2a-secreting hybridoma (American Type Culture Collection HB129, Rockville, Md.), respectively, using standard techniques with reverse transcriptase MMLV-RT (Gibco BRL, GrandIsland, N.Y.) and a synthetic oligo-dT$_{(12-18)}$ oligonucleotide (Gibco BRL). The IL-10 cDNA was then amplified by PCR using IL-10-specific synthetic oligonucleotides. The 5' oligonucleotide inserted a unique NotI restriction site 40 nucleotides 5' to the translational start codon, while the 3' oligonucleotide eliminated the termination codon and changed the C-terminal serine codon from AGC to TCG to accommodate the creation of a unique BamHI site at the IL-10/Fc junction. synthetic oligonucleotides used for the amplification of the Fcγ2a domain cDNA changed the first codon of the hinge from Glu to Asp in order to create a unique BamHI site spanning the first codon of the hinge and introduce a unique XbaI site 3' to the termination codon.

Figure 1:
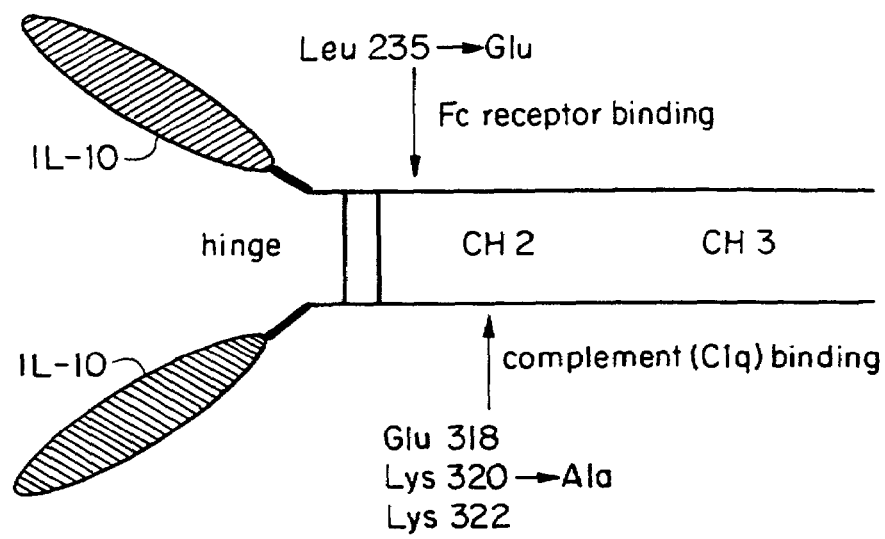

To make the construct for the non-lytic IL-10/Fc oligonucleotide, site-directed mutagenesis was used to replace Glu 318, Lys 320, and Lys 322 of the Clq binding motif of Fc with Ala residues. Similarly, Leu 235 was replaced with Glu to inactivate the FcγR I binding site. Ligation of the IL-10 and Fcγ2a components in the correct translational reading frame at the unique BamHI site yielded a 1,236 bp long open reading frame encoding a single 411 amino acid polypeptide (including the 18 amino acid IL-10 signal peptide) with a total of 13 cysteine residues (FIG. 1). The mature, secreted homodimeric IL-10/Fc is predicted to have a total of up to eight intramolecular and three inter-heavy chain disulfide linkages, and a molecular weight of 90.1 kD, not accounting for glycosylation.

Expression and Purification of IL-10/Fc: Proper genetic construction of both IL-10/Fc++ (carrying the wild-type Fcγ2a sequence) and IL-10/Fc was confirmed by DNA sequence analysis following cloning of the fusion genes as NotI—XbaI cassettes into the eukaryotic expression plasmid pRc/CMV (Invitrogen, San Diego, Calif.). This plasmid carries a CMV promoter/enhancer, a bovine growth hormone polyadenylation signal, and a neomycin resistance gene for selection against G418. Plasmids carrying the IL-l0/Fc++ or IL-10/Fc fusion genes were transfected into Chinese Hamster Ovary cells (CHO-K1) by electroporation (1.5 kV/3 μF/0.4 cm/PBS) and selected in serum-free Ultra-CHO media (BioWhittaker Inc., Walkerville, Md.) containing 1.5 mg/ml of G418. (Geneticin, Gibco BRL). After subcloning, clones which produced the chimeric protein at high levels were selected by screening supernatants by ELISA for IL-10. IL-10/Fc and IL-10/FC++ chimeric proteins were purified from culture supernatants by protein-A sepharose affinity chromatography followed by dialysis against PBS and 0.22 μm filter sterilization. Purified proteins were stored at −20° C. until they were used.

Confirmation of Size, and IL-10 and Fcγ2a Isotype Specificity: Western blot analysis following SDS-PAGE under reducing (+DTT) and non-reducing (−DTT) conditions was performed using monoclonal anti-murine IL-10 (PharMingen) or polyclonal anti-murine Fcγ primary antibodies (Pierce, Rockford, Ill.). As is shown in FIG. 2, the IL-10/Fc chimeric proteins each migrated under reducing (+DTT) conditions as a single species at the expected molecular size of 45 kD. Under non-reducing (−DTT) conditions, each IL-10/Fc migrated as a single species having a molecular size of 91 kD, indicating that the chimeric proteins assembled as homodimers. Moreover, the IL-10/Fc fusion proteins bound both anti-mIL-10 mAb (FIG. 2B) and anti-mIgG heavy chain polyclonal antibodies (FIG. 2A), confirming the cytokine specificity of the IL-10 moiety and the isotype specificity of the Fcγ2a domain.

Standardization of the Biological Activity of rIL-10 and IL-10/Fc: Using the same RT-PCR strategy and the 5' NotI sense oligonucleotide primer described above, mIL-10 cDNA with an XbaI restriction site added 3' to its native termination codon was cloned into pRc/CMV. This construct was then transiently expressed in COS cells by the DEAE dextran method and grown in serum-free UltraCulture media (BioWhittaker Inc.). At day 5, the culture supernatant was sterilized and stored at −20° C. to provide a source of recombinant IL-10 (rIL-10). Using a standard curve based on commercially supplied rIL-10 (PharMingen), IL-10/Fc and rIL-10 concentrations were determined by ELISA and then by bioassay. The unit activity based on ELISA corresponded with that obtained in a standard IL-10 bioassay, which utilized a murine mast cell line (MC/9) with rIL-4 (PharMingen) as a co-stimulant (see, e.g., Thompson-Snipes et al., 1991, J. Exp. Med. 173:507).

Figure 3:
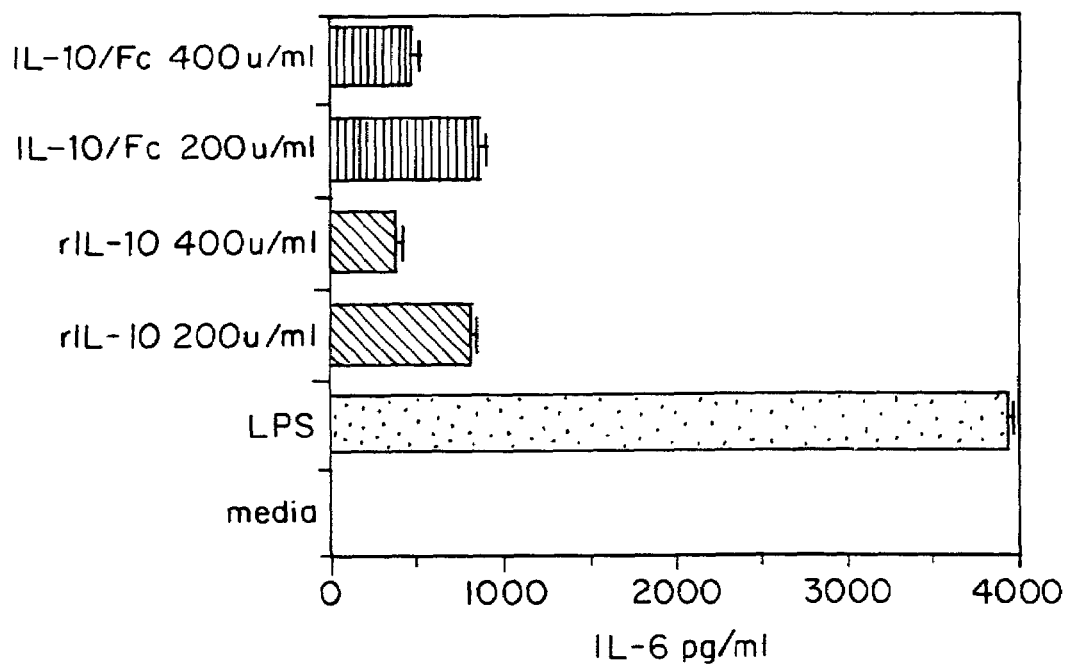

In Vitro Characterization of IL-10/Fc: IL-10/Fc functional activity was assessed in two independent assays. First, the ability of IL-10/Fc to inhibit IL-6 secretion by LPS-stimulated macrophages was measured. In this assay, IL-6 levels in supernatants of cultures of murine monocyte/macrophage PU5-1.8 cells that were stimulated in the absence or presence of varying doses of rIL-10 or IL-10/Fc was measured by ELISA (see, e.g., Fiorentino et al., 1991, J. Immunol. 147:3815). As is shown in FIG. 3, IL-10/Fc inhibits LPS-induced IL-6 secretion by PU5-1.8 cells in a dose-dependent manner.

Figure 4:
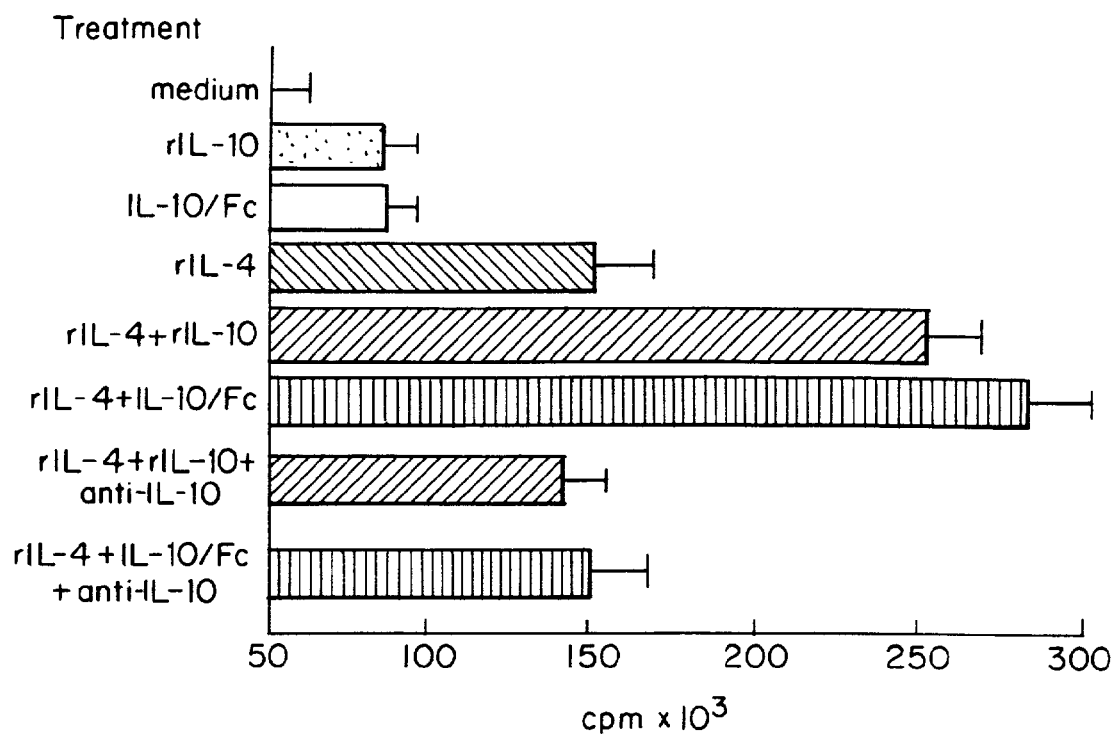

The ability of IL-10 to enhance IL-4-dependent growth of MC/9 mast cells was also assayed. In this assay, I measured incorporation of [$^3$H]-thymidine into MC/9 cells that were grown in 100 U/ml of rIL-10 or IL-10/Fc and in the presence or absence of a neutralizing anti-murine IL-10 mAb (Biosource International, Camarillo, Calif.; see, e.g., Thompson-Snipes, 1991, J. Exp. Med. 173:507). FcγR I binding assays were performed with CHO-K1 cells that had been transfected with human FcγR I cDNA. The murine CHO cells which lacked FCγR I, FCγR II, and IL-10 receptors were transfected by electroporation with 20 μg of PvuI-linearized pRc/CMV carrying cDNA encoding human FcγR I. CHO/FcγR I cells (5×10$^5$) were washed twice with FCM buffer (PBS containing 0.1% FCS (BioWhittaker Inc.) and 0.1% sodium azide) and then incubation with 10 μg/ml of murine IgG2a (Cappel, West Chester, Pa.), IL-10/Fc, or IL-10/Fc++. After incubation for 60 minutes on ice, the cells were harvested and washed in FCM buffer and then incubated with fluorescein conjugated polyclonal goat-anti-mouse IgG Fc antibody for 60 minutes in the dark. The cells were washed and stored in a 1% formalin/PBS solution at 4° C. and then analyzed on a FACStar cell sorter (Becton-Dickinson, San Jose, Calif.). The data presented in FIG. 4 demonstrate that, as was previously noted with rIL-10, IL-10/Fc enhances the IL-4-dependent growth of the murine mast cell line MC/9, and this co-stimulatory effect is blocked by a neutralizing anti-IL-10 mAb. Thus, on a mole for mole basis in terms of IL-10, IL-10/Fc possesses a biological function equivalent to that of rIL-10 in these two bioassays.

Figure 5:
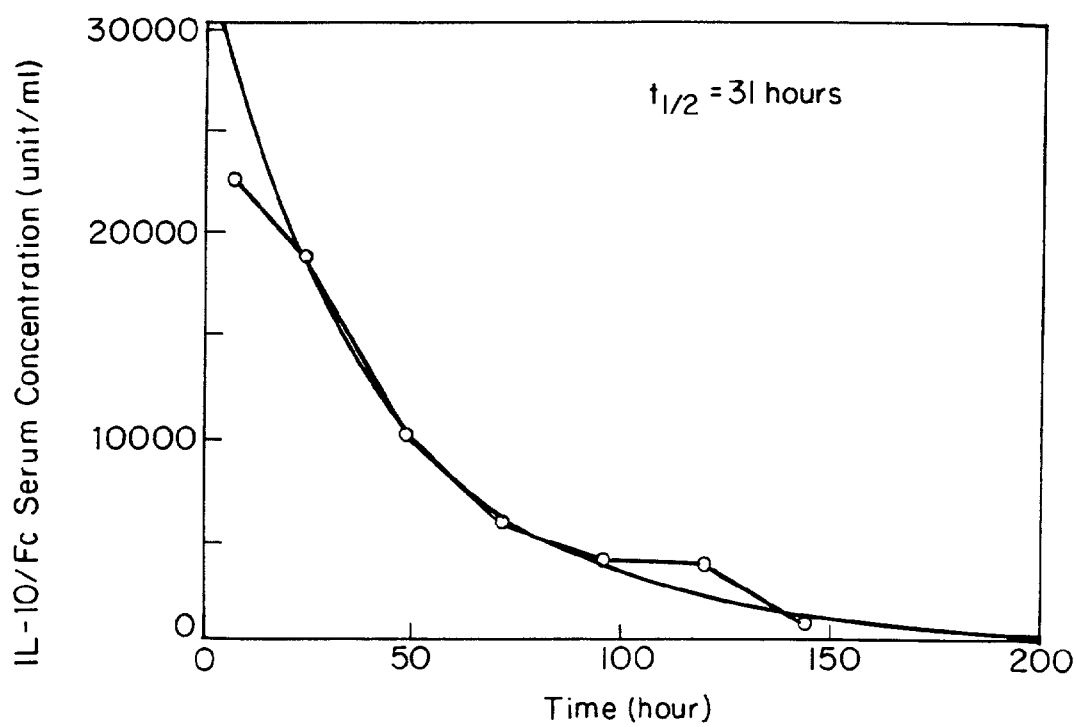
Figure 6A:
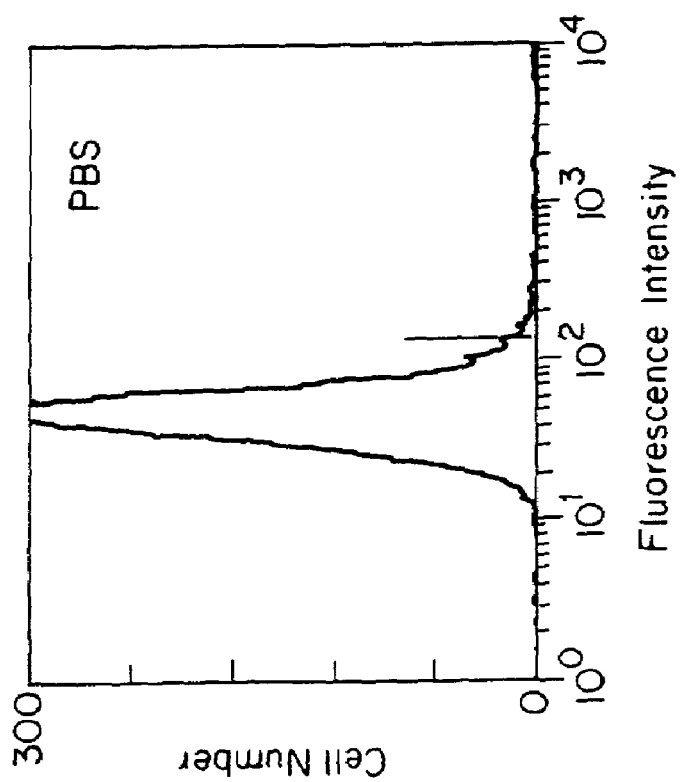
Figure 6B:
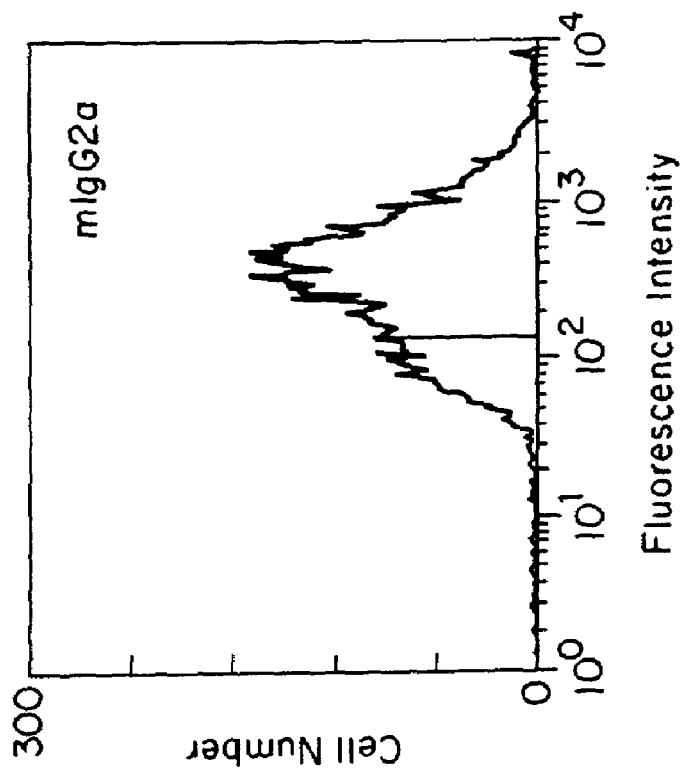
Figure 6D:
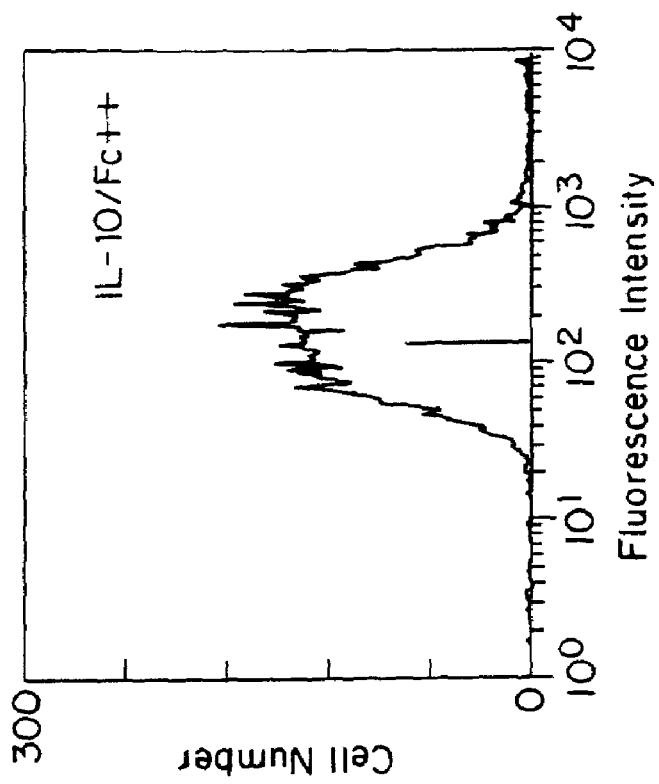
Figure 6C:
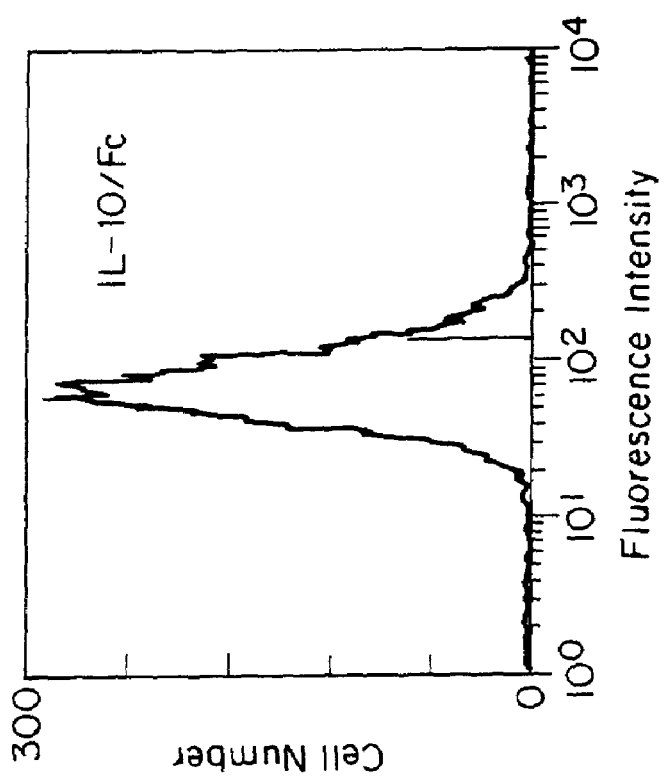

Determination of IL-10/Fc Circulating Half-life: To measure the circulating half-life of IL-10/Fc, the serum concentration of IL-10/Fc was determined over time following a single bolus intravenous injection of the chimeric protein into each of six 8- to 10-week old BALB/c mice (Jackson Laboratory). Serial 100 µl blood samples were obtained by retro-orbital bleeding at 0.1, 6, 24, 48, 72, and 96 hours after administration of IL-10/Fc to the mice. Measurements of the IL-10/Fc circulating half-life were made in an ELISA with a rat-anti-mouse IL-10 mAb as the capture antibody and a horseradish peroxidase conjugated rat-anti-mouse Fcγ2a monoclonal antibody as the detection antibody (PharMingen), thus assuring that this assay was specific for IL-10/Fc and not IL-10 or mIgG2a. The circulating half-life of IL-10/Fc was determined to be 31 hours (FIG. 5). Thus IL-10/Fc possesses the biological functions of IL-10 and a prolonged circulating half-life. Furthermore, due to the specific mutations introduced into the Fcγ2a CH2 domain, the FcγR I binding abilities have been drastically attenuated (FIG. 6) (see, e.g., Duncan et al., 1988, Nature 332–563). In addition, I have found that the mutation in the C1q binding site greatly diminishes the ability of the Fcγ2a domain to activate complement. Therefore, the ability of IL-10/Fc to support CDC has been eliminated.

LPS-induced Septic Shock: To measure the ability of IL-10/Fc to treat or inhibit septic shock, eight-to ten-week old BALB/c female mice were treated with IL-10/Fc, rIL-10, mIgG2a, or PBS prior to intravenous injection of 500 µg LPS into each mouse. A total of twenty-four animals received either 2,000 U of IL-10/Fc (12 animals) or 2,000 U of rIL-10 (12 animals) by intraperitoneal injection 30 minutes before administration of LPS. In a second experiment, each of 12 animals received 4,000 U of IL-10/Fc or rIL-10 24 hours before administration of LPS. In control experiments, animals were treated with equivalent mass concentrations of mIgG2a (n=6) or equivalent volumes of PBS (n=12) given 30 minutes before administration of LPS. Survival was the endpoint measurement.

Figure 7:
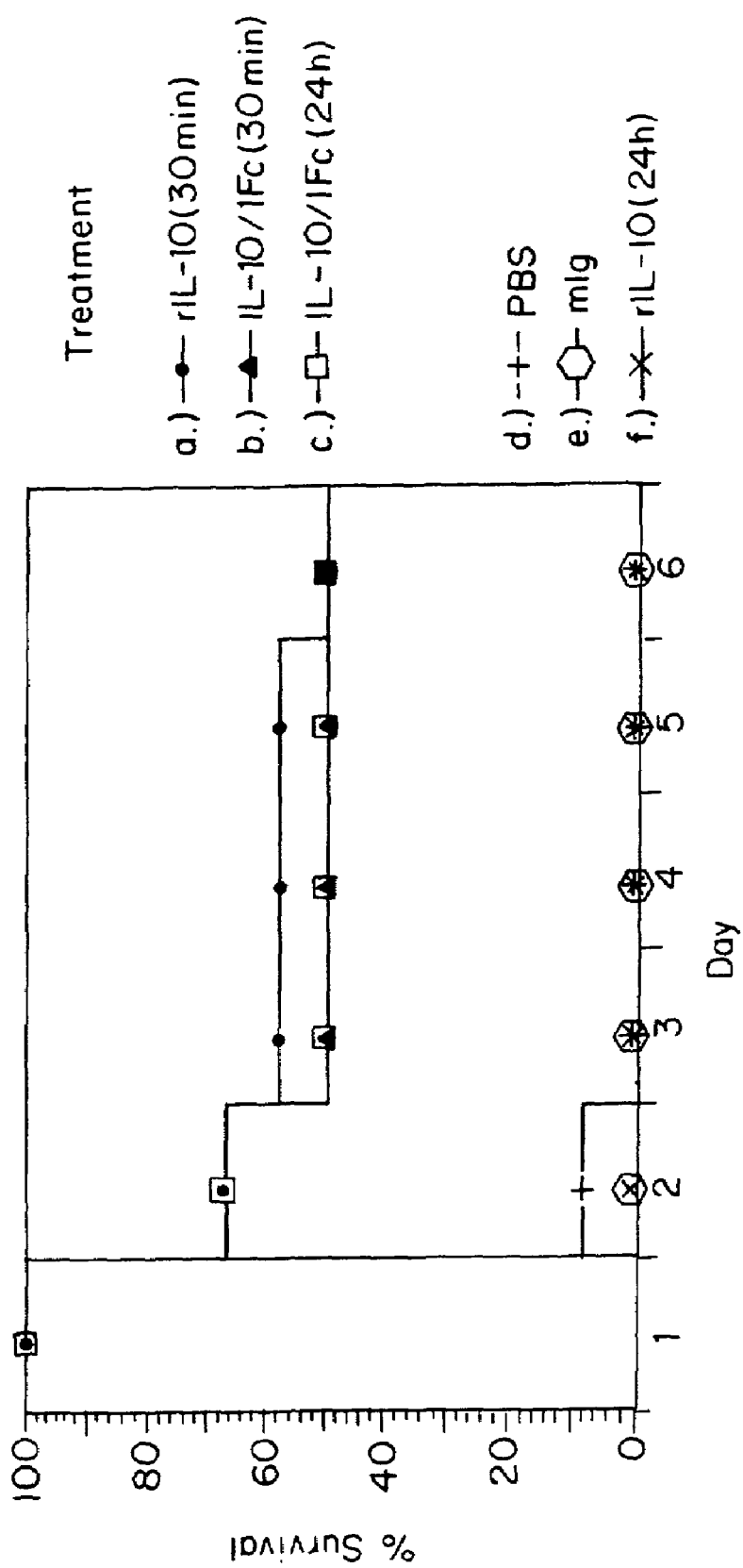

As is shown in FIG. 7, a single dose of 500 µg LPS was uniformly lethal within 72 hours in animals that were treated with PBS or mIgG2a. Mice that were treated with 2,000 U of rIL-10 or IL-10/Fc 30 minutes before LPS challenge had a 50% survival rate. All of the mice that were treated with 4,000 U of rIL-10 24 hours prior to LPS challenge died, while 50% of mice pretreated with 4,000 U of IL-10/Fc survived. These data indicate that IL-10/Fc and rIL-10 provide similar levels of protection from the lethal effect of LPS when they are given 30 minutes prior to an LPS injection. In contrast to rIL-10, IL-10/Fc confers prolonged protection, even when it is administered 24 hours prior to challenge with LPS. This finding is consistent with the longer circulating half-life of IL-10/Fc relative to rIL-10. Thus, these data indicate that a chimeric molecule of the invention provides long-term protection against septic shock in a known animal model of the disease.

Figure 8:
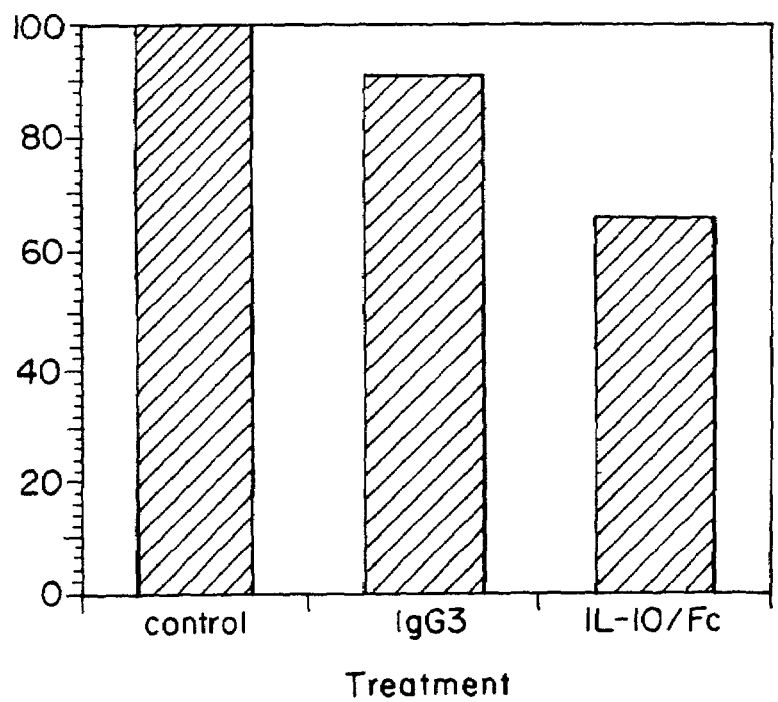
FIG. 8 is a histogram which indicates that IL-10/Fc down-regulates granuloma size in livers of Schistosome-infected mice.

IL-10/Fc Down-regulates Granuloma Formation in Schistosome-infected Mice: I have also found that IL-10/Fc inhibits schistosome-induced granuloma formation in animals. In these studies, female C57BL/6 mice were infected with 60 cercariae of *Schistosoma mansoni* (Puetro Rico strain). After four weeks of infection, the mice were randomly divided into three experimental groups:
  (i) 5 mice which received no treatment;
  (ii) 5 mice which were treated with mIgG3; and
  (iii) 5 mice which were treated with IL-10/Fc. After four weeks of Schistosome infection, mice in groups (ii) and (iii) were treated by intraperitoneal injection of mIgG3 or IL-10/Fc as follows: 2 µg/mouse on day 1 of treatment, and then 1 µg/mouse every day for three weeks. After 7 weeks of Schistosome infection, the mice in all three experimental groups were sacrificed. The mice livers were then fixed in formalin, processed with conventional histopathologic techniques, and then 5-µm sections were stained with hematoxylin and eosin. Granulomatous inflammation was assessed quantitatively with computer-assisted morphometric analysis. As is indicated by FIG. 8, treatment with IL-10/Fc inhibited granuloma formation in the livers of mice. Accordingly, the data obtained with this animal model of Schistosome infection indicate that IL-10/Fc can be used to inhibit granuloma formation in animals.

Prevention or Inhibition of Diabetes with IL-10/Fc: The chimeric IL-10 proteins of the invention are useful for treating or inhibiting the development of Type I diabetes in a patient. The following detailed examples employ a well-known animal model of human diabetes, the non-obese diabetic (NOD) mouse. To study the effects of IL-10/Fc on diabetes, a total of 30 mice were divided into three experimental groups:
  (i) 10 mice which received no treatment;
  (ii) 10 mice which were treated with mIgG3; and
  (iii) 10 mice which were treated with IL-10/Fc. Treatment was initiated when the mice reached 5 weeks of age. Treatment of mice in groups (ii) and (iii) involved intraperitoneal injection of 2 µg of mIgG3 or IL-10/Fc on day 1, followed by intraperitoneal injection of 1 µg of mIgG3 or IL-10/Fc every second day until the mice reached 19 weeks of age. Diabetes was diagnosed with conventional methods and criteria.

Figure 9:
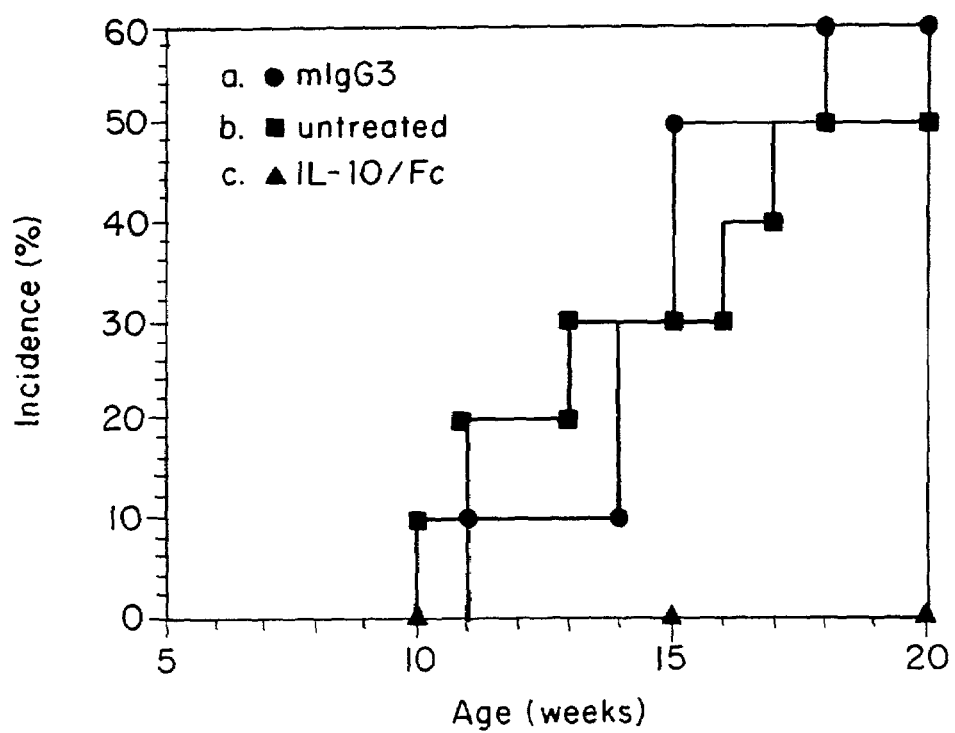
FIG. 9 is a graph which shows that IL-10/Fc prevents the onset of diabetes in non-obese diabetic (NOD) mice.

As is indicated in FIG. 9, at least 50% of the control mice (mIgG3-treated and untreated mice) developed diabetes during the 20 weeks of the study. In contrast, the onset of diabetes during the course of the study was completely prevented in mice that had been treated with IL-10/Fc. These data, obtained with an art-recognized model of human diabetes, indicate that IL-10/Fc is useful for preventing or inhibiting the onset of diabetes in animals (e.g., humans).

The usefulness of IL-10/Fc in inhibiting the onset of diabetes was re-affirmed in an additional experiment with NOD mice. A total of 19 mice were divided into three experimental groups:
  (i) 6 mice which received no treatment;
  (ii) 7 mice which were treated with mIgG2a; and
  (iii) 6 mice which were treated with IL-10/Fc. For mice in groups (ii) and (iii), treatment was initiated when the mice were 6 weeks of age. The treatment regimen included intraperitoneal injection of 2 µg of mIgG2a or IL-10/Fc on day 1, followed by intraperitopeal injection of 1 µg of mIgG2a or IL-10/Fc every second day until the mice reached 25 weeks of age. Diabetes was diagnosed using conventional methods and criteria.

Figure 10:
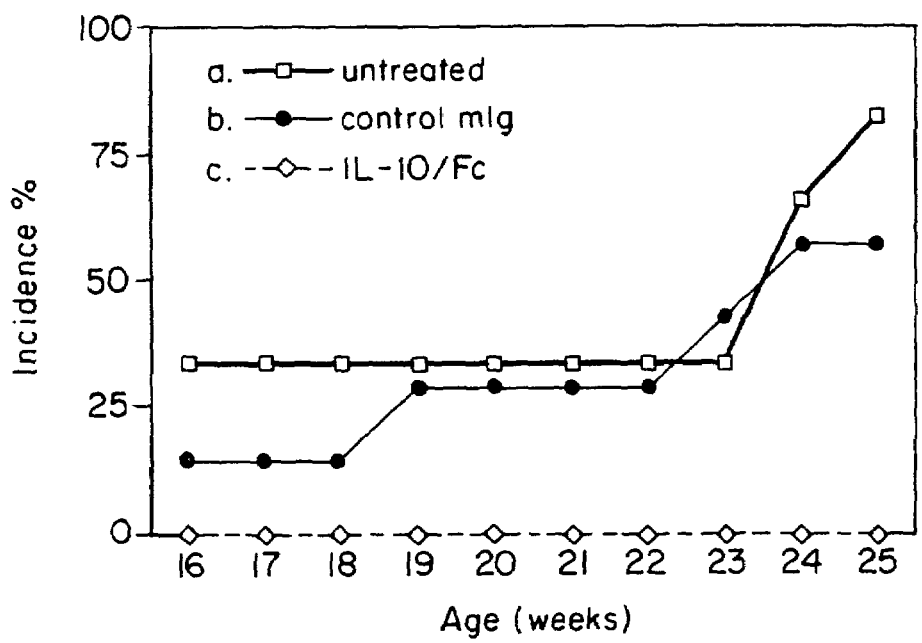
FIG. 10 is a graph which indicates that IL-10/Fc prevents the onset of diabetes in NOD mice.

As is shown in FIG. 10, at least 50% of the mice in the control groups (untreated mice and mIgG2a-treated mice) developed diabetes before reaching 25 weeks of age. In marked contrast, none of the IL-10/Fc-treated mice developed diabetes. At 52 weeks of age, 84% of the animals which had been treated with IL-10/Fc continued to have normal glucose levels (i.e., they did not develop diabetes) despite the cessation of therapy. These data, obtained with an art-recognized animal model of human diabetes, indicate that IL-10/Fc is useful for preventing or inhibiting the onset of diabetes. These-data also indicate that IL-10/Fc provides long-term protection against diabetes.

Further evidence that IL-10/Fc is useful for treating diabetes comes from my finding that mice treated with IL-10/Fc bear suppressor (anti-diabetogenic) lymphocytes.

This beneficial effect has not been reported for mammals treated with the non-chimeric IL-10 molecule. In this experiment, 25 ten- to twelve-week old male NOD mice (i.e., the recipients) were irradiated (700 Rads) to impair their immune systems. The mice were then divided into four experimental groups:

(i) 9 recipients which were treated with a mixture of $30 \times 10^6$ splenic cells from acutely diabetic female NOD mice and $30 \times 10^6$ splenic cells from 11-week old untreated co-donors;

(ii) 7 recipients which were treated with a mixture of $30 \times 10^6$ splenic cells from acutely diabetic female NOD mice and $30 \times 10^6$ splenic cells from 11-week old co-donors that had been treated with mIgG3;

(iii) 5 recipients which were treated with a mixture of $30 \times 10^6$ splenic cells from acutely diabetic female NOD mice and $30 \times 10^6$ splenic cells from 11-week old co-donors that had been treated with IL-10/Fc; and (iv) 4 recipients which were treated with a mixture of $30 \times 10^6$ splenic cells from acutely diabetic female NOD mice and $30 \times 10^6$ splenic cells from 54-week old co-donors that had been treated with IL-10/Fc.

Treatment of NOD mice was initiated when the mice reached 5 weeks of age and included intraperitoneal injection of 2 μg of mIgG3 or IL-10/Fc on day 1 of treatment, followed by injection of 1 μg of mIgG3 or IL-10/Fc every second day until the mice reached 25 weeks of age. Some of the treated mice were used as cell donors to test for the presence of suppressive type immune phenomena that could be detected in cell transfer work.

Figure 11:
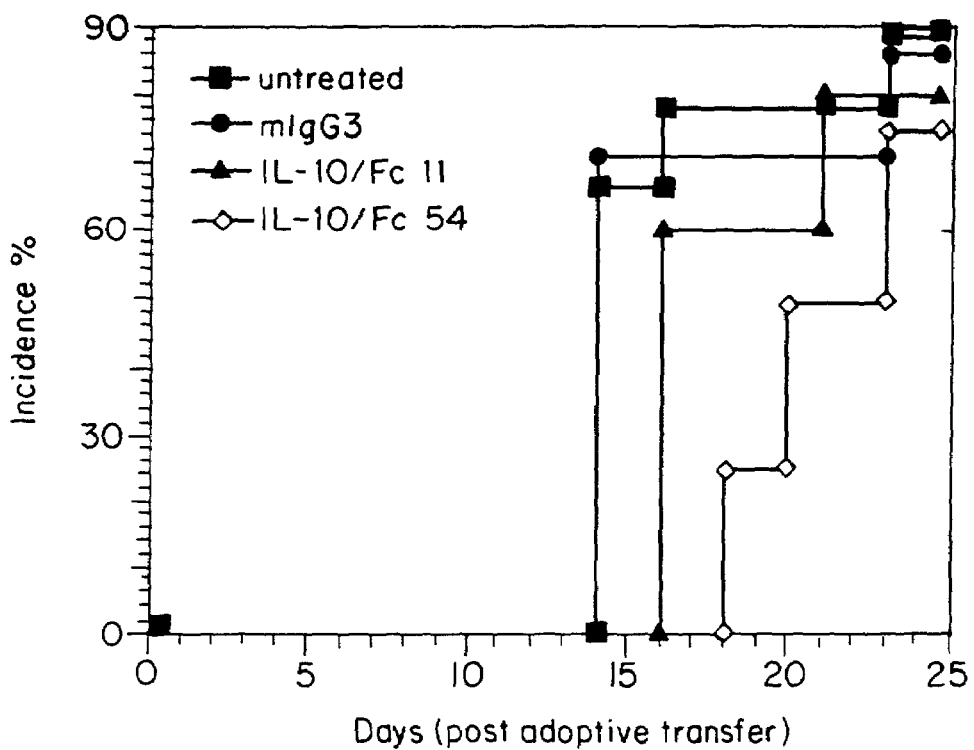
FIG. 11 is a graph which indicates that mice treated with IL-10/Fc bear suppressor (anti-diabetogenic) lymphocytes.

Diabetes was diagnosed with conventional methods and criteria. As is indicated in FIG. 11, greater than 85% of NOD mice that received splenic cells from untreated or mIgG3-treated co-donors developed diabetes within 25 days of transfer of the splenic cells. The development of diabetes was inhibited in mice that had been treated with IL-10/Fc from 11- or 54-week old co-donors. These data indicate that the onset of diabetes in an animal can be inhibited by transferring into the animal splenic cells that have been treated with IL-10/Fc. Thus, not only are the remissions caused by chimeric IL-10 (e.g., IL-10/Fc) long-lasting in contrast to the temporary effect seen with non-chimeric IL-10, the remissions are associated with the formation of anti-diabetogenic suppressive immune phenomena that have not been noted with non-chimeric IL-10 treatment.

Treatment or Prevention of Granuloma Formation with IL-4/Fc

I have found that treatment of mice with IL-4/Fc inhibits the formation of granulomas that normally are formed when a mammal is infected with Schistosoma. Accordingly, IL-4/Fc can be used to inhibit granulomatous inflammation in a patient and to inhibit or prevent schistosomiasis.

Genetic Construction of IL-4/Fc: Complementary DNAs for murine IL-4 and murine Fcγ2a were generated from mRNA extracted from Con A-stimulated murine splenic cells (C57BL/6J; Jackson Laboratory, Bar Harbor, Me.) and an IgG2a-secreting hybridoma (American Type Culture Collection HB129, Rockville, Md.), respectively, using standard techniques with reverse transcriptase MMLV-RT (Gibco BRL, Grand Island, N.Y.) and a synthetic oligo-dT$_{(12-18)}$ oligonucleotide (Gibco BRL).

To make the construct for the non-lytic IL-4/Fc oligonucleotide, site-directed mutagenesis was used to replace Glu 318, Lys 320, and Lys 322 of the C1q binding motif of Fc with Ala residues. Similarly, Leu 235 was replaced with Glu to inactivate the FcγR I binding site (FIG. 12).

Expression and Purification of IL-4/Fc: Proper genetic construction of IL-4/Fc was confirmed by DNA sequence analysis-following cloning of the fusion genes into the eukaryotic expression plasmid pRc/CMV (Invitrogen, San Diego, Calif.). This plasmid carries a CMV promoter/enhancer, a bovine growth hormone polyadenylation signal, and a neomycin resistance gene for selection against G418. Plasmids carrying the IL-4/Fc fusion genes were transfected into Chinese Hamster Ovary cells (CHO-K1) by electroporation (1.5 kV/3 μF/0.4 cm/PBS) and selected in serum-free Ultra-CHO media (BioWhittaker Inc., Walkerville, Md.) containing 1.5 mg/ml of G418 (Geneticin, Gibco BRL). After subcloning, clones which produced the chimeric protein at high levels were selected by screening supernatants by ELISA for IL-4. The IL-4/Fc chimeric protein was purified from culture supernatants by protein-A sepharose affinity chromatography followed by dialysis against PBS and 0.22 μm filter sterilization. The purified protein was stored at −20° C. until it was used.

CTLL-2 Proliferation Assay with IL-4/Fc: The function of the IL-4 portion of IL-4/Fc was assayed in a conventional CTLL-2 proliferation assay. In such an assay, the addition of IL-4 to a culture induces the cells to proliferate, and proliferation can be detected by assaying for the incorporation of [$^3$H] into the cells. The data obtained in this optional assay of IL-4/Fc function indicate that cell proliferation in response to IL-4/Fc substantially parallels cell proliferation in response to recombinant IL-4 over a range of concentrations (FIG. 13).

Determination of IL-4/Fc Circulating Half-life: I have found that the circulating half-life of IL-4 can be extended by bonding IL-4 to a non-lytic Fc region of IgG. In this experiment, the time-related serum concentration of non-lytic IL-4/Fc was determined following a single bolus intravenous injection (8 mg) of IL-4/Fc into mice (FIG. 14). Blood samples were obtained by retro-orbital bleeding of the mice. Non-lytic IL-4/Fc levels were then measured in an ELISA with rat-anti-mouse IL-4 monoclonal antibodies as the capture antibodies and horseradish peroxidase-conjugated rat anti-mouse IgG heavy chain monoclonal antibodies as the detection antibodies. These data indicate that the circulating half-life of IL-4/Fc is approximately 25 hours.

IL-4/Fc Inhibits Schistosome Granuloma Formation in vivo: Female C57BL/6 mice were infected with 60 cercariae of *Schistosoma mansoni* (Puetro Rico strain). After four weeks of infection, the mice were randomly divided into three groups:

(i) 5 mice which received no treatment;

(ii) 5 mice which were treated with mIgG3; and (iii) 5 mice which were treated with IL-4/Fc. After four weeks of Schistosome infection, mice in groups (ii) and (iii) were treated by intraperitoneal injection of mIgG3 or IL-4/Fc, respectively, as follows: 2,500 U/mouse on day 1 of treatment, and then 1,250 U/mouse every day for three weeks. After 7 weeks of Schistosome infection, the mice in all three experimental groups were sacrificed. The mice livers were then fixed in formalin, processed with conventional histopathologic techniques, and then 5-μm sections were stained with hematoxylin and eosin. Granulomatous inflammation was assessed quantitatively by computer-assisted morphometric analysis. As is indicated by FIG. 15, treatment with IL-4/Fc inhibited granuloma formation in the livers of mice. Accordingly, the data obtained with this animal model of Schistosome infection indicate that IL-4/Fc can be used to inhibit granuloma formation in animals (e.g., humans).

Other embodiments are within the following claims. For example, virtually any mutation can be used to disable the complement-fixing capability of the Fc region of an antibody.

What is claimed is:

1. A chimeric protein comprising interleukin-10 (IL-10) and a polypeptide that increases the circulating half-life of the chimeric protein comprising IL-10 relative to that of IL-10 alone.

2. The chimeric protein of claim 1, wherein the polypeptide comprises a hinge region of an IgG molecule.

3. The chimeric protein of claim 1, wherein the polypeptide comprises albumin.

4. The chimeric protein of claim 1, wherein the polypeptide comprises the Fc region of an IgG molecule but lacks an IgG variable region.

5. The chimeric protein of claim 4, wherein the polypeptide further comprises a hinge region of an IgG molecule.

6. The chimeric protein of claim 4, wherein the Fc region is lytic.

7. The chimeric protein of claim 4, wherein the Fc region is non-lytic.

8. The chimeric protein of claim 4, wherein the Fc region comprises a mutation that inhibits complement fixation and high affinity binding to the Fc receptor by the chimeric protein.

9. A composition comprising the chimeric protein of claim 1 and a pharmaceutically acceptable carrier.

10. The chimeric protein of claim 1, wherein the polypeptide has a molecular weight of at least 10 kDa or a net neutral charge at pH 6.8.

11. The chimeric protein of claim 1, wherein the polypeptide is a human polypeptide.

12. The chimeric protein of claim 1, wherein the polypeptide comprises a porcine or rodent glycosyltransferase or α-1,3-galactosyltransferase.

13. The composition of claim 9, wherein the pharmaceutically acceptable carrier is saline.

14. A composition comprising the chimeric protein of claim 4 and a pharmaceutically acceptable carrier.

15. The composition of claim 13, wherein the pharmaceutically acceptable carrier is saline.

* * * * *

UNITED STATES PATENT AND TRADEMARK OFFICE
CERTIFICATE OF CORRECTION

PATENT NO.        : 7,018,626 B2                                         Page 1 of 1
APPLICATION NO. : 10/145517
DATED             : March 28, 2006
INVENTOR(S)       : Terry B. Strom, Xin Xiao Zheng and Alan W. Steele It is certified that error appears in the above-identified patent and that said Letters Patent is hereby corrected as shown below:

On Title Page item 56

Page 2, OTHER PUBLICATIONS, reference Nicholas Landolfi, et al.:
   delete "Il-211" and replace with --IL-2/Ig--

Page 2, OTHER PUBLICATIONS, reference Alexander R. Duncan, et al.:
   delete "IgGNature" and replace with --IgG. Nature--

Signed and Sealed this

Twentieth Day of March, 2007

JON W. DUDAS
*Director of the United States Patent and Trademark Office*